(12) United States Patent
Ohta et al.

(10) Patent No.: US 7,764,765 B2
(45) Date of Patent: Jul. 27, 2010

(54) CASSETTE AND MOBILE X-RAY IMAGE CAPTURING APPARATUS

(75) Inventors: Yasunori Ohta, Kanagawa (JP); Eiichi Kito, Kanagawa (JP); Tsuyoshi Tanabe, Kanagawa (JP); Takuya Yoshimi, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 0 days.

(21) Appl. No.: 12/219,598

(22) Filed: Jul. 24, 2008

(65) Prior Publication Data

US 2009/0028295 A1 Jan. 29, 2009

(30) Foreign Application Priority Data

| Jul. 24, 2007 | (JP) | ............................. 2007-192076 |
| Aug. 16, 2007 | (JP) | ............................. 2007-212243 |
| Jun. 12, 2008 | (JP) | ............................. 2008-153998 |
| Jun. 12, 2008 | (JP) | ............................. 2008-154112 |

(51) Int. Cl.
H05G 1/08 (2006.01)
H05G 1/64 (2006.01)

(52) U.S. Cl. ..................... 378/91; 378/98.8; 378/189; 378/198; 250/370.09

(58) Field of Classification Search .................. 378/91, 378/98.8, 102, 189, 198; 250/370.09
See application file for complete search history.

(56) References Cited

U.S. PATENT DOCUMENTS

| 6,972,411 B2* | 12/2005 | Schick et al. .......... 250/370.11 |
| 6,999,558 B2* | 2/2006 | Okoda ........................ 378/102 |
| 7,015,478 B2* | 3/2006 | Yamamoto ............. 250/370.09 |
| 7,016,467 B2* | 3/2006 | Brooks ........................ 378/102 |
| 7,242,005 B2* | 7/2007 | Funabashi .............. 250/370.01 |
| 7,250,608 B2* | 7/2007 | Ozeki ..................... 250/370.08 |
| 7,309,159 B2* | 12/2007 | Watanabe .................... 378/198 |
| 7,365,337 B2* | 4/2008 | Tsuchino et al. ....... 250/370.09 |
| 7,545,914 B2* | 6/2009 | Kito et al. ................... 378/98.8 |
| 7,561,668 B2* | 7/2009 | Ohta et al. .................. 378/102 |
| 7,593,507 B2* | 9/2009 | Ohta et al. ................. 378/98.8 |

FOREIGN PATENT DOCUMENTS

| JP | 07-140255 | 6/1995 |
| JP | 2000-105297 | 4/2000 |
| JP | 2004-141473 | 5/2004 |
| JP | 2005-013310 | 1/2005 |

\* cited by examiner

*Primary Examiner*—Allen C. Ho
(74) *Attorney, Agent, or Firm*—Jean C. Edwards, Esq.; Akerman Senterfitt

(57) ABSTRACT

A cassette allows radiation image information stored therein to be used immediately after an X-ray radiation image is captured in a patient's room, and a mobile X-ray image capturing apparatus incorporates such a cassette. The mobile X-ray image capturing apparatus has a cradle serving as a mount for receiving the cassette which has a radiation detector. The mobile X-ray image capturing apparatus captures a radiation image of the patient (subject) in the patient's room. The cassette serves as a mobile station. While the cassette (mobile X-ray image capturing apparatus) is moving, the radiation image information stored in the cassette is transmitted to a server via a transmitting and receiving terminal, a mobile hospital communication network, and a hospital LAN.

8 Claims, 16 Drawing Sheets

CASSETTE AND MOBILE X-RAY IMAGE CAPTURING APPARATUS

CROSS-REFERENCE TO RELATED APPLICATIONS

The present application claims priority from Japanese Patent Application Nos. 2007-192076, filed Jul. 24, 2007, 2007-212243, filed Aug. 16, 2007, 2008-15998, filed Jun. 12, 2008, and 2008-154112, filed Jun. 12, 2008 the contents of all of which are herein incorporated by reference in their entirety.

BACKGROUND OF THE INVENTION

1. Field of the Invention

The present invention relates to a cassette having a radiation conversion panel for detecting a radiation that has passed through a subject and converting the detected radiation into radiation image information, and a mobile X-ray image capturing apparatus which uses such a cassette.

2. Description of the Related Art

In the medical field, there have widely been used radiation image capturing apparatus which apply a radiation to a subject and guide the radiation that has passed through the subject to a radiation conversion panel, which capture a radiation image from the radiation. Known forms of the radiation conversion panel include a conventional radiation film for recording a radiation image by way of exposure, and a stimulable phosphor panel for storing a radiation energy representing a radiation image in a phosphor and reproducing the radiation image as stimulated light by applying stimulating light to the phosphor. The radiation film with the recorded radiation image is supplied to a developing device to develop the radiation image, or the stimulable phosphor panel is supplied to a reading device to read and obtain the radiation image as a visible image.

In the operating room or the like, it is necessary to read out a recorded radiation image immediately from a radiation conversion panel after the radiation image is captured for the purpose of quickly and appropriately treating the patient. As a radiation conversion panel which meets such a requirement, there has been developed a radiation detector having a solid-state detector for converting a radiation directly into an electric signal or converting a radiation into visible light with a scintillator and then converting the visible light into an electric signal to read a detected radiation image.

In recent years, there have been growing demands for capturing an image of a critically ill patient who cannot easily be moved out of his or her room and also for capturing an image in emergency in an operating room. As a result, there have been increasing needs for apparatus which allow surgeons or doctors to confirm, quickly with high image quality, images that have been captured in clinical and surgical environments other than X-ray image capturing rooms.

To meet such needs, mobile X-ray image capturing apparatus have been proposed as disclosed in Japanese Laid-Open Patent Publication No. 2004-141473 and Japanese Laid-Open Patent Publication No. 2005-013310.

According to the mobile X-ray image capturing apparatus disclosed in Japanese Laid-Open Patent Publication No. 2004-141473, the radiation image of a patient is captured and the radiation image information is recorded in a cassette having a radiation detector, and the recorded radiation image information is transferred from the cassette via an external interface to a storage medium or a display unit by way of wireless communications immediately after the radiation image information is captured. Alternatively, the cassette with the radiation image information recorded therein is carried to a room where images can be displayed, and only the cassette is connected to a display unit or a storage medium in the room and the radiation image information is transferred from the cassette to the display unit or the storage medium.

According to the mobile X-ray image capturing apparatus disclosed in Japanese Laid-Open Patent Publication No. 2005-013310, the radiation image information of a patient is captured and recorded in a cassette, and the cassette is carried to a position within the communication range of a cassette box, whereupon the cassette automatically starts transferring the radiation image information to the cassette box.

The mobile X-ray image capturing apparatus may be required to store the radiation image information of a plurality of patients or a plurality of pieces of radiation image information of a single patient in an image memory in the cassette.

Since the radiation image information has a large volume of data, the image memory in the cassette needs to be of a large storage capacity for storing the radiation image information of plural patients or the plural pieces of radiation image information of a single patient.

There has been a demand for the quick transmission of radiation image information that has been recorded in the cassette in an image capturing site by the mobile X-ray image capturing apparatus, to a radiation image information archival facility such as a server or the like without delay.

SUMMARY OF THE INVENTION

It is an object of the present invention to provide a cassette which is capable of transmitting a plurality of items of radiation image information to a radiation image information collecting facility such as a server or the like without delay even if the storage capacity of an image memory incorporated in the cassette is small, and a mobile X-ray image capturing apparatus which uses such a cassette.

Another object of the present invention is to provide a mobile X-ray image capturing apparatus which is capable of transmitting radiation image information captured in a cassette at an image capturing site by the mobile X-ray image capturing apparatus to a radiation image information collecting facility without delay, and which is capable of using a small, lightweight cassette.

A cassette according to the present invention includes a radiation detector for detecting a radiation that has passed through a subject and converting the detected radiation into radiation image information, an image memory for storing the converted radiation image information therein, a transmitting and receiving terminal, and a controller for controlling the radiation detector, the image memory, and the transmitting and receiving terminal, wherein the transmitting and receiving terminal serves as a mobile station and communicates with a radiation image information collecting facility through a mobile communication network, and when the controller detects that the radiation image information is stored in the image memory, the controller transmits the radiation image information stored in the image memory to the radiation image information collecting facility via the transmitting and receiving terminal and the mobile communication network, while the cassette is moving.

When the controller of the cassette detects that the radiation image information is stored in the image memory, the controller transmits the radiation image information stored in the image memory to the radiation image information collecting facility via the transmitting and receiving terminal and the mobile communication network, while the cassette is moving. Therefore, the radiation image information can be utilized quickly after it is captured.

After the radiation image information is sent to the radiation image information collecting facility, new radiation image information can be stored in the image memory again. While the cassette is moving next time, the radiation image information newly stored in the image memory can be transmitted to the radiation image information collecting facility via the transmitting and receiving terminal and the mobile communication network. Accordingly, a plurality of items of radiation image information can be transmitted to the radiation image information collecting facility (server) without delay.

If the mobile communication network includes a plurality of base stations having partially overlapping communication ranges, and the transmitting and receiving terminal comprises a mobile terminal capable of sending and receiving signals by way of wireless communications, such as a PHS terminal, for example, then an existing communication infrastructure can be used. The mobile terminal may instead be a terminal having the same radio-wave oscillation intensity as PHS terminals.

According to the present invention, there is also provided a mobile X-ray image capturing apparatus including a mount for detachably attaching the above cassette thereon and supplying electric power to the cassette.

The cassette may be loaded in the mount of the mobile X-ray image capturing apparatus, and may be moved to a room where an image is to be captured, e.g., an operating room, a patient's room, a diagnosis and treatment room, a home care room, that is, a room other than an X-ray room. After radiation image information is captured in the cassette, the cassette is loaded in the mount of the mobile X-ray image capturing apparatus. While the mobile X-ray image capturing apparatus is moving, the captured radiation image information can be transmitted from the transmitting and receiving terminal of the cassette to the radiation image information collecting facility, using electric power supplied from the mobile X-ray image capturing apparatus.

According to the present invention, there is also provided a mobile X-ray image capturing apparatus for capturing a radiation image of a subject in a room where an image is captured, comprising a radiation source for applying a radiation to the subject, a mount for receiving therein a cassette having a radiation detector for detecting a radiation having passed through the subject and converting the detected radiation into radiation image information and storing the radiation image information, an image memory, a transmitting and receiving terminal, and a controller for controlling the radiation source, the mount, the image memory, and the transmitting and receiving terminal, wherein the transmitting and receiving terminal serves as a mobile station and communicates with a radiation image information collecting facility through a mobile communication network, and when the controller detects that the radiation image information is stored in the cassette mounted in the mount, the controller transmits the radiation image information from the cassette via the mount to the image memory for storing the radiation image information therein, and while the mobile X-ray image capturing apparatus is moving, the controller transmits the radiation image information stored in the image memory to the radiation image information collecting facility via the transmitting and receiving terminal and the mobile communication network.

When the controller of the mobile X-ray image capturing apparatus detects that the radiation image information is stored in the cassette mounted in the mount of the mobile X-ray image capturing apparatus, the controller transmits the radiation image information from the cassette via the mount to the image memory for storing the radiation image information therein, and while the mobile X-ray image capturing apparatus is moving, the controller transmits the radiation image information stored in the image memory to the radiation image information collecting facility via the transmitting and receiving terminal and the mobile communication network. Accordingly, the cassette is not required to have a wireless communication function and hence may have a small power requirement. The cassette can thus be small in size and weight and can be carried around with ease.

In as much as the radiation image information is sent to the radiation image information collecting facility (server) while the mobile X-ray image capturing apparatus is moving, the radiation image information can be utilized quickly after the radiation image information is captured.

The mobile X-ray image capturing apparatus further includes an exit detecting mechanism for detecting that the mobile X-ray image capturing apparatus has moved out of the room. Since the controller starts transmitting the radiation image information to the radiation image information collecting facility when the exit detecting mechanism detects that the mobile X-ray image capturing apparatus has moved out of the room, radio waves are not transmitted or received in the room where the image has been captured.

The mobile communication network includes a plurality of base stations having partially overlapping communication ranges, and the transmitting and receiving terminal comprises an existing mobile terminal, i.e., a PHS terminal, mounted in the mobile X-ray image capturing apparatus and capable of sending and receiving signals by way of wireless communications. Accordingly, an existing communication infrastructure can be used without the need for a new communication infrastructure for use between the mobile X-ray image capturing apparatus and the radiation image information collecting facility. The mobile terminal may instead be a terminal having the same radio-wave oscillation intensity as PHS terminals.

The room where the image is captured may comprise a room other than an X-ray room, for example, an operating room, a patient's room, a diagnosis and treatment room, or a home care room.

Even if the storage capacity of the image memory of the cassette is small, the mobile X-ray image capturing apparatus can send a plurality of items of radiation image information to the radiation image information collecting facility (server) without delay.

According to the present invention, the mobile X-ray image capturing apparatus is capable of transmitting the radiation image information captured in the cassette at the image capturing site by the mobile X-ray image capturing apparatus to the radiation image information collecting facility without delay. The mobile X-ray image capturing apparatus can use a small, lightweight cassette.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Figure 1:
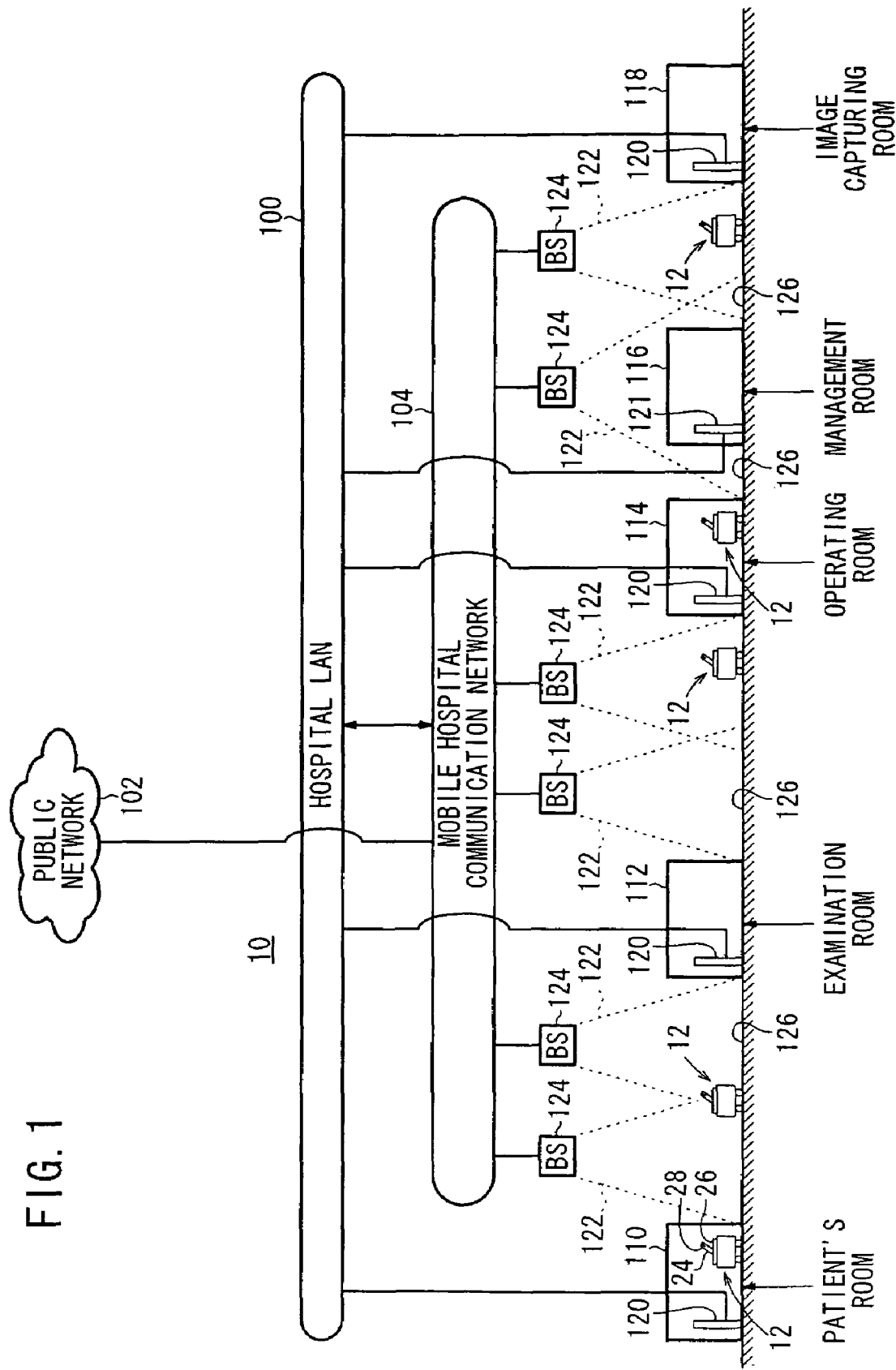
FIG. 1 is a schematic diagram, partly in block form, of a hospital radiation image information collecting system incorporating a plurality of mobile X-ray image capturing apparatus according to an embodiment of the present invention.

Like or corresponding parts are denoted by line or corresponding reference characters throughout views.

FIG. 1 shows a hospital radiation image information collecting system 10 incorporating a plurality of mobile X-ray image capturing apparatus 12 according to an embodiment of the present invention. Each of the mobile X-ray image capturing apparatus 12 is used with a cassette 24 according to an embodiment of the present invention, and includes a cradle (mount) 26 for receiving the cassette 24 removably therein.

The mobile X-ray image capturing apparatus 12 are movable in a patient's room 110, aisles 126, an examination room (diagnosis and treatment room) 112, an operating room 114, a management room 116, and an image capturing room (X-ray room, radiological room) 118 in a hospital.

The hospital radiation image information collecting system 10 has two communication networks including a hospital LAN (hospital communication network) 100 for use as an intranet and a mobile hospital communication network 104 connected to a public network 102. The hospital LAN 100 and the mobile hospital communication network 104 are connected to each other for mutual data communications.

The hospital LAN 100 is connected to consoles (including computers) 120 that serves as controllers respectively in the patient's room 110, the examination room 112, the operating room 114, and the image capturing room 118 which houses a fixed X-ray image capturing apparatus, not shown, and is also connected to a server (controller) 121 which can be used as both a collecting facility and a console in the management room 116. The server 121 generally manages radiation image information handled in a radiology department of the hospital and other information, for example.

A plurality of base stations 124, which are connected to the mobile hospital communication network 104, are disposed and the base stations 124 have respective communication ranges 122 such that the communication ranges 122 of adjacent ones of the base stations 124 overlap each other.

The communication ranges 122 of the base stations 124 do not extend into the patient's room 110, the examination room 112, the operating room 114, and the image capturing room 118, but the communication ranges 122 of some of the base stations 124 cover the management room 116 and the aisles 126.

Figure 2:
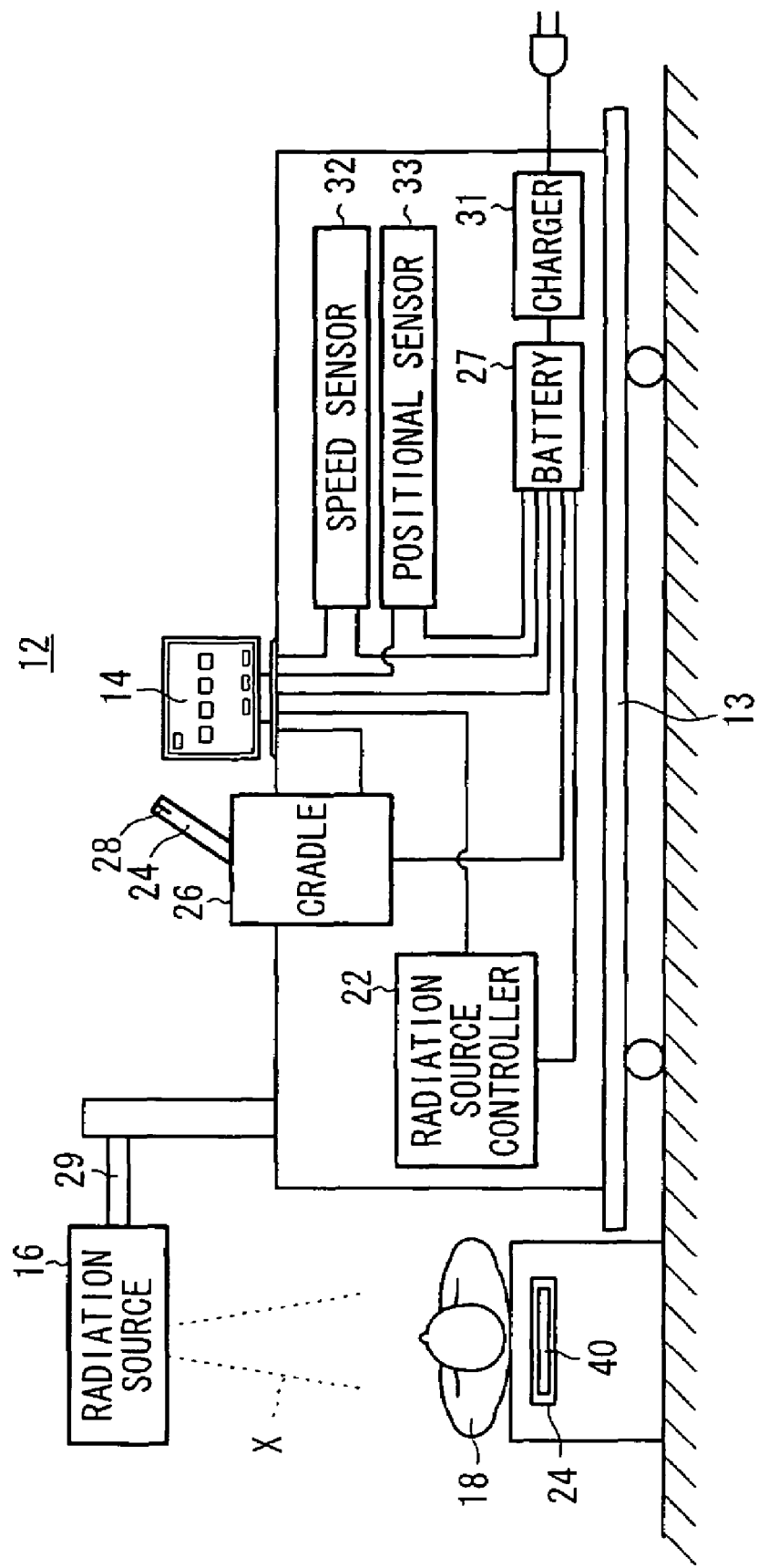
FIG. 2 is a schematic diagram, partly in block form, showing the manner in which one of the mobile X-ray image capturing apparatus shown in FIG. 1 is used in a patient's room, for example.

FIG. 2 shows the manner in which one of the mobile X-ray image capturing apparatus 12 is used in the patient's room 110, for example. As shown in FIG. 2, the mobile X-ray image capturing apparatus 12 is integrally placed on a carriage 13 so as to be movable into the patient's room 110.

The mobile X-ray image capturing apparatus 12 placed on the carriage 13 includes a console 14 having a display for entering image capturing information or the like for capturing radiation image information, a radiation source controller 22 for controlling a radiation source 16 according the image capturing information supplied from the console 14 to apply a radiation X to a subject, e.g., a patient 18, the cradle (cassette mount) 26 for receiving the cassette 24 which houses a radiation detector 40 for recording radiation image information of the patient 18 when it is irradiated with the radiation X that has passed through the patient 18, and a battery 27. The battery 27 supplies electric power to the console 14, the radiation source 16, the radiation source controller 22, and the cassette 24 via the cradle 26.

The radiation source 16 is coupled to the radiation source controller 22 by an arm 29. The battery 27 can be charged by a charger 31 connected thereto.

The carriage 13 also carries thereon a speed sensor 32 for detecting whether or not the carriage 13 moves, and a positional sensor 33 such as a GPS or the like for detecting the position of the carriage 13.

Figure 3:
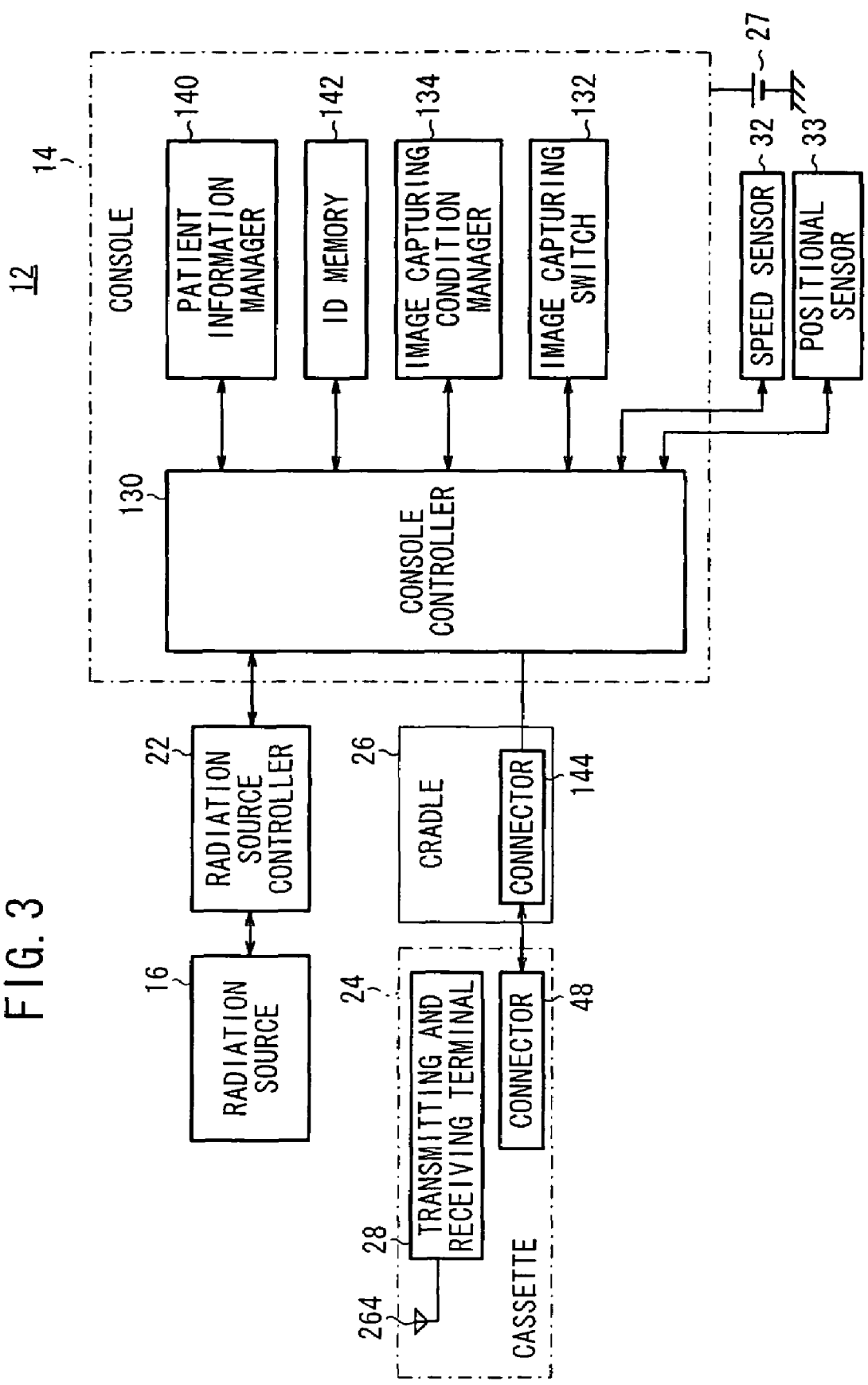
FIG. 3 is a functional block diagram of a console of the mobile X-ray image capturing apparatus.

FIG. 3 shows in function block form the console 14 of the mobile X-ray image capturing apparatus 12. The console 14 comprises a console controller 130, an image capturing switch 132, an image capturing condition manager 134 for managing image capturing conditions required for capturing radiation images based on the radiation X from the radiation source 16, a patient information manager 140 for managing patient information of the subject (patient) 18 whose image is to be captured, and an ID memory 142 for storing ID information for identifying the mobile X-ray image capturing apparatus 12. The speed sensor 32 and the positional sensor 33 are connected to the console controller 130.

The image capturing conditions refer to condition for determining a tube voltage, a tube current, an irradiation time, etc. required to apply a radiation X at an appropriate dose to an area of the patient 18 to be imaged. The image capturing conditions may include an area of the patient 18 to be imaged, an image capturing method, etc., for example. The patient information refers to information for identifying the patient 18, such as the name, gender, patient ID number, etc. of the patient 18. Ordering information for instructing the mobile X-ray image capturing apparatus 12 to capture a radiation image, including the image capturing conditions and the patient information, can be set directly on the console 14 or can be acquired in advance from the server 121 via the hospital LAN 100 through a cable, not shown, by which the console 14 is connected to the console 120 in the patient's room 110 or the like.

The console controller 130 is connected to the cradle 26 by a connector 144 thereof. When the cassette 24 is mounted in the cradle 26, the cassette 24 is electrically connected to the connector 144 by a connector 48 thereof. The console controller 130 supplies electric power from the battery 27 to the cassette 24 through the connectors 144, 48, and communicates with the cassette 24 through a cassette controller 46 (see FIG. 6) thereof.

Figure 4:
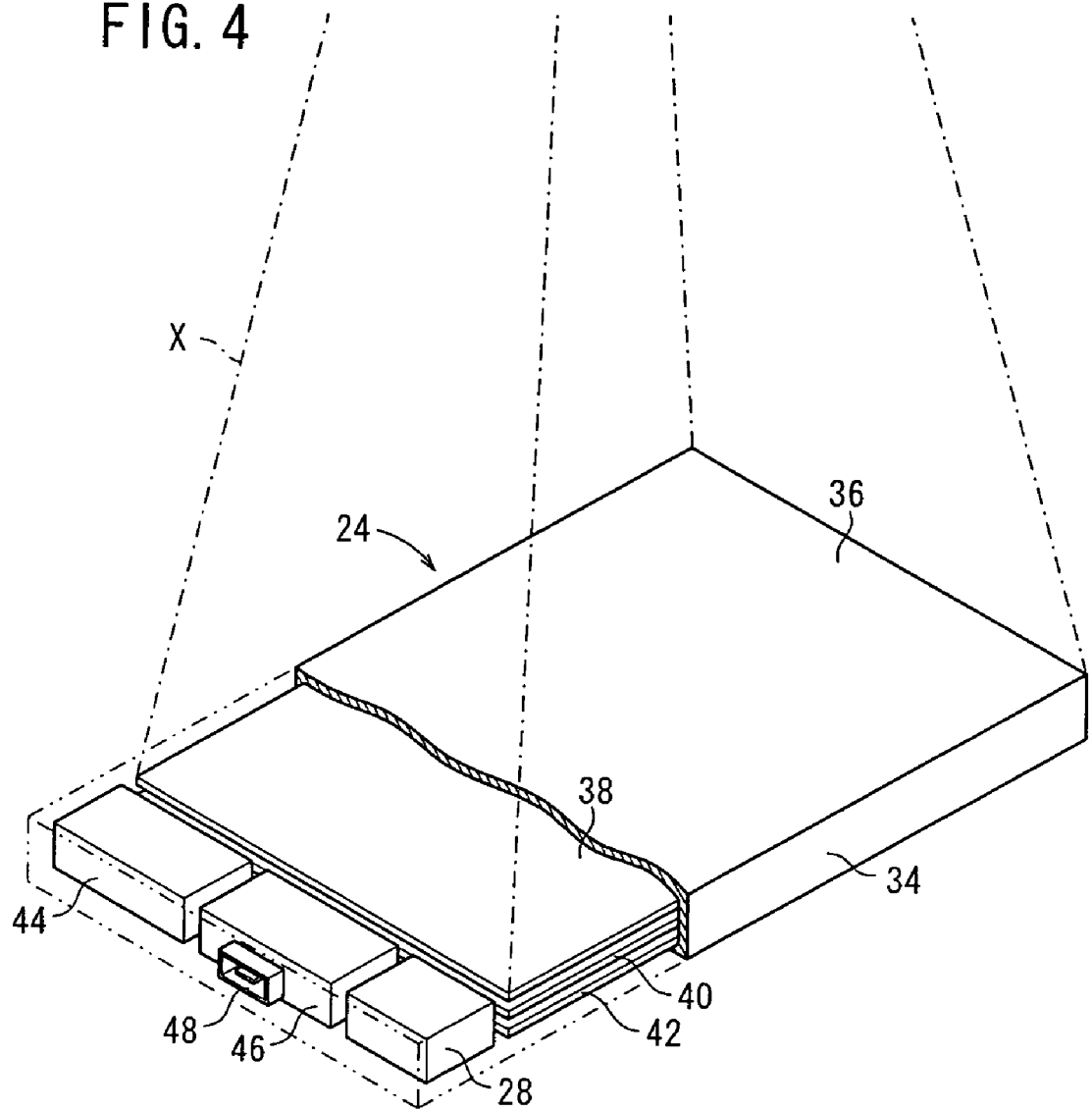
FIG. 4 is a perspective view, partly cut away, showing internal structural details of a cassette according to an embodiment of the present invention.

FIG. 4 shows in perspective internal structural details of the cassette 24. As shown in FIG. 4, the cassette 24 has a casing 34 made of a material permeable to the radiation X. The casing 34 houses therein a grid 38 for removing scattered rays of the radiation X from the patient 18, a radiation detector (radiation conversion panel) 40 for detecting the radiation X that has passed through the patient 18, and a lead plate 42 for absorbing back scattered rays of the radiation X. The grid 38, the radiation detector 40, and the lead plate 42 are successively arranged in that order named from an irradiated surface 36 of the casing 34 which is irradiated with the radiation X. The irradiated surface 36 of the casing 34 may be constructed as the grid 38.

The casing 34 also houses therein a battery 44 as a power supply of the radiation detecting cassette 24, a cassette controller 46 for energizing the radiation detector 40 with electric power supplied from the battery 44, and a transmitting and receiving terminal 28 for sending and receiving signals including the information of the radiation X detected by the radiation detector 40, to and from the server 121 in the management room 116 via the mobile hospital communication network 104. The connector 48 is mounted on the cassette controller 46. The battery 44 of the cassette 24 and a battery 268 (see FIG. 5) of the transmitting and receiving terminal 28 are charged by the battery 27 of the mobile X-ray image capturing apparatus 12 through the connector 144 (see FIG. 3), the connector 48, and the cassette controller 46. As described above, the cassette controller 46 and the console controller 130 communicate with each other through the connector 48 and the connector 144.

A shield plate of lead or the like should preferably be placed between the side surface of the cassette controller 46 and the irradiated surface 36 of the casing 34 to protect the cassette controller 46 against damage which would otherwise be caused if that were irradiated with the radiation X.

Figure 5:
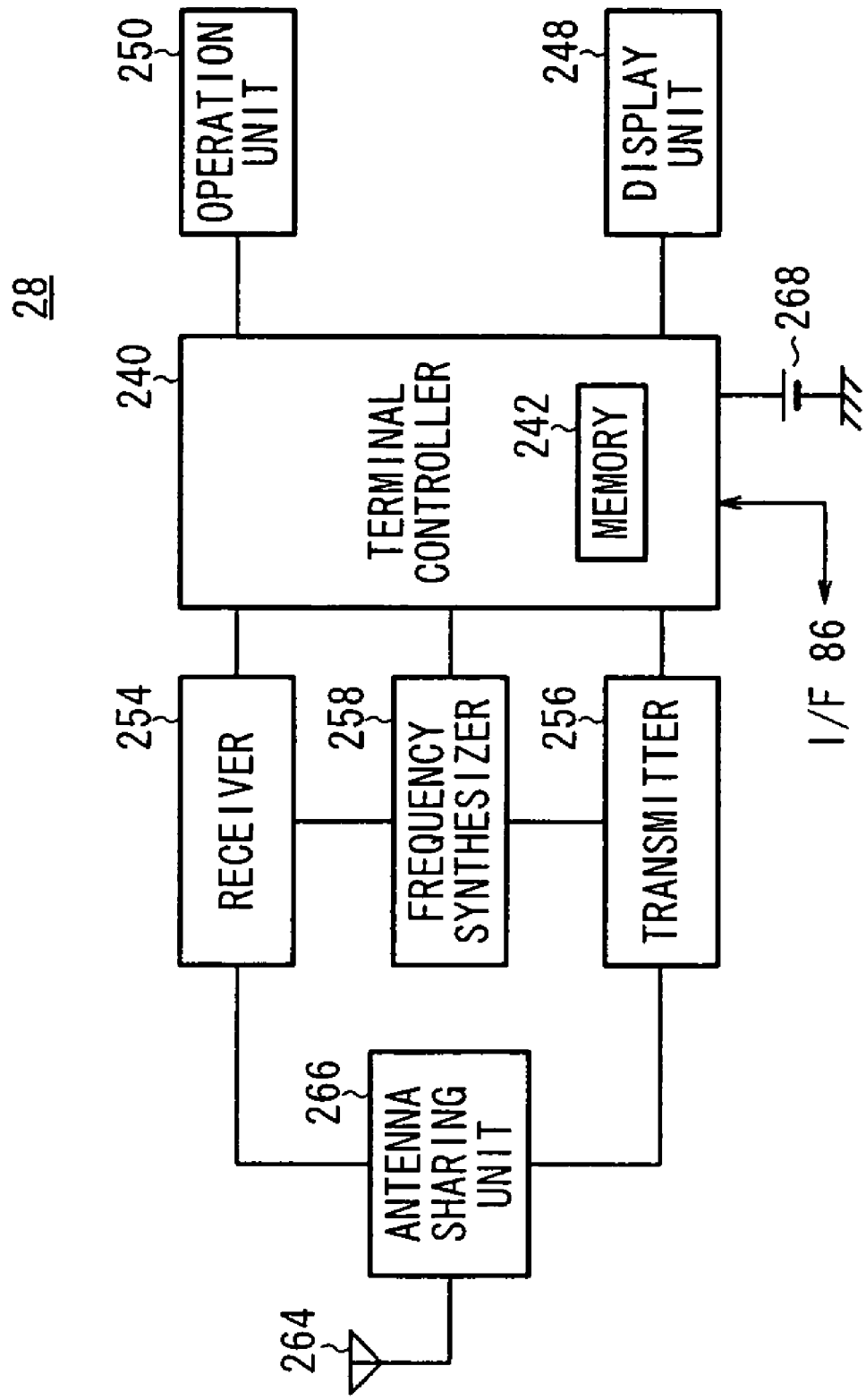
FIG. 5 is a functional block diagram of a transmitting and receiving terminal of the cassette shown in FIG. 4.

FIG. 5 shows in functional block form the transmitting and receiving terminal 28 of the cassette 24. The transmitting and receiving terminal 28 may comprise a PHS terminal which is an existing mobile terminal.

The transmitting and receiving terminal 28 comprises a battery 268 and a terminal controller 240 having a microcomputer, which comprises a CPU and a memory 242 as a nonvolatile memory such as a flash memory or the like.

An operation unit 250 having operation switches and a display unit 248 comprising a liquid crystal display are connected to the terminal controller 240. The transmitting and receiving terminal 28 should preferably be disposed in the cassette 24 such that the display unit 248 can be seen from outside.

To the terminal controller 240, there is also connected a receiver 254 for receiving radio waves (RF signal) received by an antenna 264 via an antenna sharing unit 266, converting the RF signal into an intermediate-frequency signal, demodulating the intermediate-frequency signal, and outputting the demodulated intermediate-frequency signal as received data to the terminal controller 240. The terminal controller 240 monitors a signal from the receiver 254 at constant intervals. If received data are transmitted, the terminal controller 240 controls the receiver 254 to receive the data, and displays the contents of the received data on the display unit 248.

To the terminal controller 240, there is also connected a transmitter 256 for modulating data (radiation image information or the like) read out from an image memory 82 (see FIG. 6) into an intermediate-frequency signal, converting the intermediate-frequency signal into an RF signal, and sending the RF signal through the antenna sharing unit 266 to the antenna 264, from which a radio wave based on the RF signal is radiated.

A frequency synthesizer 258 for outputting a located oscillation frequency for mixer circuits of the receiver 254 and the transmitter 256 is connected to the terminal controller 240.

Figure 6:
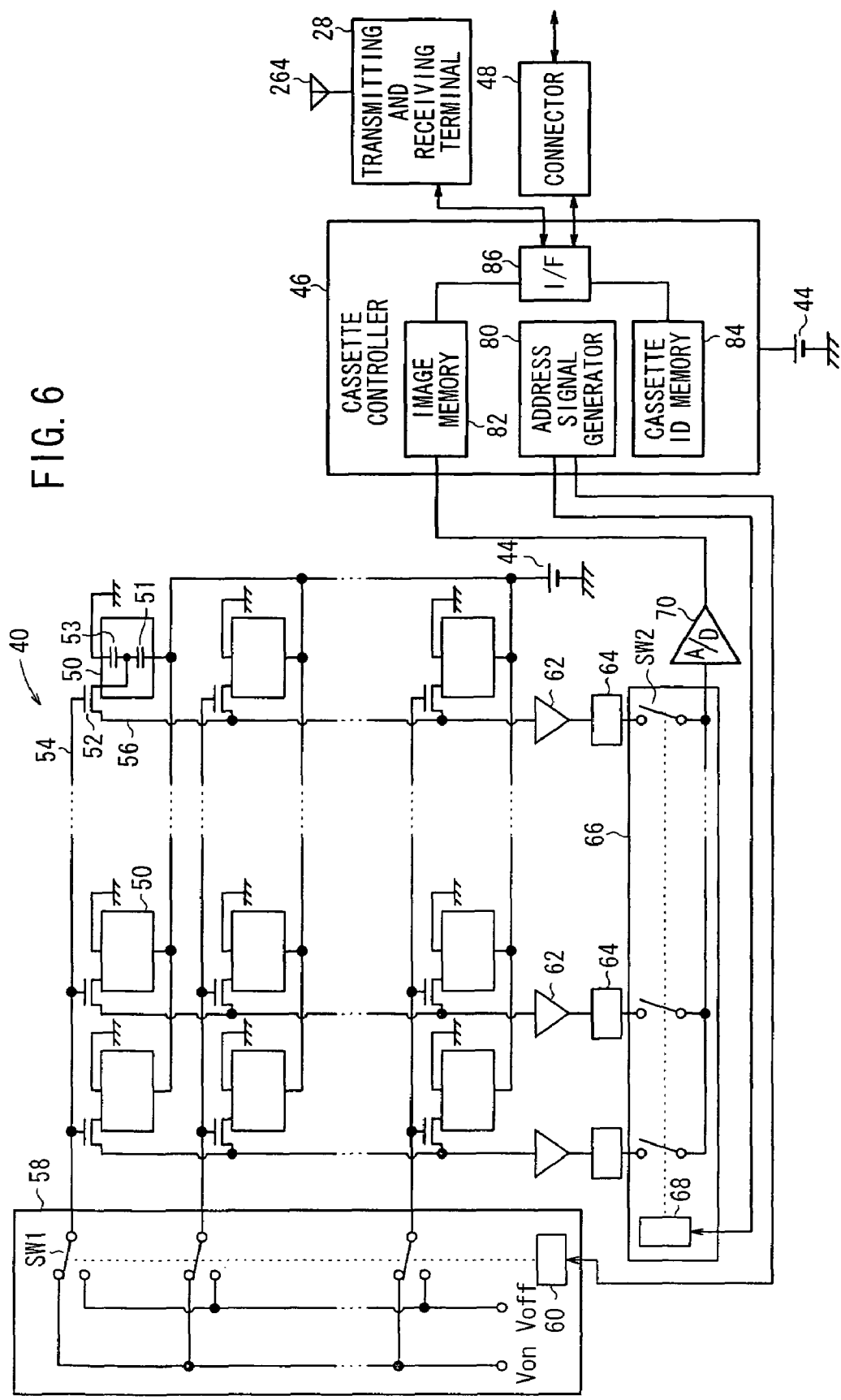
FIG. 6 is a functional block diagram of a radiation detector and a cassette controller of the cassette shown in FIG. 4.

FIG. 6 shows in block form the radiation detector 40 and the cassette controller 46 of the cassette 24. As shown in FIG. 6, the radiation detector 40 comprises an array of thin-film transistors (TFTs) 52 arranged in rows and columns, a photoelectric conversion layer 51 made of a material such as amorphous selenium (a-Se) for generating electric charges upon detection of the radiation X, the photoelectric conversion layer 51 being disposed over the array of TFTs 52, and an array of storage capacitors 53 connected to the photoelectric conversion layer 51. When the radiation X is applied to the radiation detector 40, the photoelectric conversion layer 51 generates electric charges, and the storage capacitors 53 store the generated electric charges. Then, the TFTs 52 are turned on along each row at a time to read out the electric charges from the storage capacitors 53 as an image signal. In FIG. 6, the photoelectric conversion layer 51 and one of the storage capacitors 53 are shown as a pixel 50, and the pixel 50 is connected to one of the TFTs 52. Details of the other pixels 50 are omitted from illustration. Since amorphous selenium tends to change its structure and lose its functionality at high temperatures, it needs to be used within a certain temperature range. Therefore, some means for cooling the radiation detector 40 should preferably be provided in the cassette 24.

The TFTs 52 connected to the respective pixels 50 are connected to respective gate lines 54 extending parallel to the rows and respective signal lines 56 extending parallel to the columns. The gate lines 54 are connected to a line scanning driver 58, and the signal lines 56 are connected to a multiplexer 66 serving as a reading circuit.

The gate lines 54 are supplied with control signals Von, Voff for turning on and off the TFTs 52 along the rows from the line scanning driver 58. The line scanning driver 58 comprises a plurality of switches SW1 for switching between the gate lines 54 and an address decoder 60 for outputting a selection signal for selecting one of the switches SW1 at a time. The address decoder 60 is supplied with an address signal from the cassette controller 46.

The signal lines 56 are supplied with electric charges stored in the storage capacitors 53 of the pixels 50 through the TFTs 52 arranged in the columns. The electric charges supplied to the signal lines 56 are amplified by amplifiers 62 connected respectively to the signal lines 56. The amplifiers 62 are connected through respective sample and hold circuits 64 to the multiplexer 66. The multiplexer 66 comprises a plurality of switches SW2 for switching between the signal lines 56 and an address decoder 68 for outputting a selection signal for selecting one of the switches SW2 at a time. The address decoder 68 is supplied with an address signal from the cassette controller 46. The multiplexer 66 has an output terminal connected to an A/D converter 70. A radiation image signal generated by the multiplexer 66 based on the electric charges from the sample and hold circuits 64 is converted by the A/D converter 70 into a digital image signal representing radiation image information, which is supplied to the cassette controller 46.

The cassette controller 46 comprises an address signal generator 80 for supplying address signals to the address decoder 60 of the line scanning driver 58 and the address decoder 68 of the multiplexer 66 of the radiation detector 40, an image memory 82 for storing the radiation image information detected by the radiation detector 40, a cassette ID memory 84 for storing cassette ID information for identifying the cassette 24, and an interface 86.

The interface 86 receives a transmission request signal for radiation image information via the transmitting and receiving terminal 28 and transmits the cassette ID information stored in the cassette ID memory 84 and the radiation image information stored in the image memory 82.

The cassette 24 and the hospital radiation image information collecting system 10 incorporating the mobile X-ray image capturing apparatus 12 are basically constructed as described above, and operation of the cassette 24 and the hospital radiation image information collecting system 10 will be described below.

As shown in FIG. 2, the mobile X-ray image capturing apparatus 12 is used when a radiation image of the patient 18 is required by the doctor while the doctor is visiting the patient's room 110. Before a radiation image of the patient 18 is captured, patient information of the patient 18 to be imaged is registered in the patient information manager 140 of the console 14. If an area of the patient 18 to be imaged and an image capturing method have already been known, they are registered as image capturing conditions in the image capturing condition manager 134. After the above preparatory process is finished, a radiation image of the patient 18 is captured.

For capturing a radiation image of the patient 18, the doctor or the radiological technician places the cassette 24 in a given position which faces the radiation source 16 across the patient 18 with the irradiated surface 36 facing the radiation source 16. Then, the doctor or the radiological technician turns on the image capturing switch 132 to capture a radiation image of the patient 14.

The radiation source controller 22 acquires image capturing conditions about the area of the patient 18 to be imaged from the image capturing condition manager 134 of the console 14 via the console controller 130. When the radiation source controller 22 receives the image capturing conditions, it controls the radiation source 16 to apply a radiation X at a given dose to the patient 18 according to the acquired image capturing conditions.

The radiation X which has passed through the patient 18 is applied to the grid 38, which removes scattered rays from the radiation X. Then, the radiation X is applied to the radiation detector 40, and converted into electric signals by the photoelectric conversion layer 51 of the pixels 50 of the radiation detector 40. The electric signals are stored as electric charges in the storage capacitors 53 (see FIG. 6). The stored electric charges, which represent radiation image information of the patient 18, are read out from the storage capacitors 53 according to address signals which are supplied from the address signal generator 80 of the cassette controller 46 to the line scanning driver 58 and the multiplexer 66.

Specifically, in response to the address signal supplied from the address signal generator 80, the address decoder 60 of the line scanning driver 58 outputs a selection signal to select one of the switches SW1, which supplies the control signal Von to the gates of the TFTs 52 connected to the gate line 54 corresponding to the selected switch SW1. In response to the address signal supplied from the address signal generator 80, the address decoder 68 of the multiplexer 66 outputs a selection signal to successively turn on the switches SW2 to switch between the signal lines 56 for thereby reading out the electric charges stored in the storage capacitors 53 of the pixels 50 connected through the signal lines 56 to the selected gate line 54 selected by the line scanning driver 58.

The electric charges read out from the storage capacitors 53 of the pixels 50 connected to the selected gate line 54 of the radiation detector 40 are amplified by the respective amplifiers 62, sampled by the sample and hold circuits 64, and supplied to the multiplexer 66. Based on the supplied electric charges, the multiplexer 66 generates and supplies a radiation image signal to the A/D converter 70, which converts the radiation image signal into a digital signal. The digital signal which represents the radiation image information is temporally stored in the image memory 82 of the cassette controller 46.

Similarly, the address decoder 60 of the line scanning driver 58 successively turns on the switches SW1 to switch between the gate lines 54 according to the address signal supplied from the address signal generator 80. The electric charges stored in the storage capacitors 53 of the pixels 50 connected to the successively selected gate lines 54 are read out through the signal lines 56, and processed by the multiplexer 66 and the A/D converter 70 into digital signals. The digital signals which represent the radiation image information are stored in the image memory 82 of the cassette controller 46.

After having captured the radiation image information, the cassette 24 is placed in the cradle 26 of the mobile X-ray image capturing apparatus 12.

When the connectors 48, 144 are connected to each other at this time, the console controller 130 supplies the patient information of the patient 18 registered in the patient information manager 140 to the interface 86 via the connectors 144, 48. The interface 86 associates the radiation image information stored in the image memory 82 with the supplied patient information, and stores the radiation image information associated with the supplied patient information in the image memory 82.

Thereafter, the interface 86 will permit the radiation image information to be transferred through the transmitting and receiving terminal 28 to the mobile hospital communication network 104. Since the patient's room 110 is not covered by the communication range 122 of the corresponding base stations 124, the transmitting and receiving terminal 28 does not send the radiation image information as long as the mobile X-ray image capturing apparatus 12 is positioned in the patient's room 110.

When the mobile X-ray image capturing apparatus 12 moves out of the patient's room 110 and the cassette 24 (the transmitting and receiving terminal 28 thereof) enters the communication range 122 of the corresponding base stations 124, or, in other words, when the transmitting and receiving terminal 28 detects a predetermined radio-wave intensity from the base station 124, the transmitting and receiving terminal 28 indicates the detection of the predetermined radio-wave intensity to the interface 86 (the cassette controller 46).

The interface 86 then reads out the radiation image information from the image memory 82 and transfers the read radiation image information to the terminal controller 240 of the transmitting and receiving terminal 28. The terminal controller 240 sends the radiation image information sent from the image memory 82 via the interface 86 to the base station 124 through the antenna sharing unit 266 and the antenna 264. The base station 124 transfers the received radiation image information to the server 121 in the management room 116 via the mobile hospital communication network 104 and the hospital LAN 100.

The radiation image information transferred to the server 121 in the management room 116 can immediately be sent through the hospital LAN 100 and used for examination by the doctor or the like who handles the console 120 in the examination room 112, for example.

As shown in FIG. 1, since the communication ranges 122 of adjacent ones of the base stations 124 overlap each other while the mobile X-ray image capturing apparatus 12 is moving down the aisle or aisles 126 from the patient's room 110 to the examination room 112 or to another patient's room 110, not shown, the mobile X-ray image capturing apparatus 12 can switch successively to communication ranges 122 of greater radio-wave intensities. Accordingly, the mobile X-ray image capturing apparatus 12 can transfer the radiation image information reliably to the server 121 without communication interruptions while being in motion down the aisle or aisles 126. When the mobile X-ray image capturing apparatus 12 captures radiation image information in the next patient's room 110, the captured radiation image information can thus be stored in the image memory 82 of the same cassette 24, by overwriting any existing radiation image information. The image memory 82 of the cassette 24 is usually of a storage capacity for recording the radiation image information only for a sheet of radiation image.

Therefore, even though the storage capacity of the image memory 82 of the cassette 24 is small, i.e., can store only the radiation image information for one image capturing, the mobile X-ray image capturing apparatus 12 can send the radiation image information of patients 18 in a plurality of patient's rooms 110 to the server 121 as a radiation image collecting facility without delay.

Instead of determining whether the cassette 24 is in the patient's room 110 or not, i.e., whether or not the cassette 24 has moved out of the patient's room 110, based on the communication ranges 122, an exit detecting mechanism for detecting whether the cassette 24 has moved out of the patient's room 110 or not may comprise an RFID card attached to the cassette 24 and an RFID card reader attached to the patient's room 110 near its door. The cassette 24 may be detected as moving out of the patient's room 110 when the RFID card reader detects a radio wave radiated from the RFID card attached to the cassette 24.

The cassette 24 may also be detected as moving if the console controller 130 judges that the mobile X-ray image capturing apparatus 12 is moving based on a signal from the speed sensor 32 and/or the positional sensor 33 at the time the cassette 24 is connected to the console 14 through the cradle 26.

According to the above embodiment, as described above, the mobile X-ray image capturing apparatus 12 includes the radiation source 16, the cradle 26 serving as a mount for the cassette 24 which includes the radiation detector 40 for detecting the radiation X that has emitted from the radiation source 16 and passed through the patient (subject) 18, and storing the detected radiation image information, and the console controller 130 for controlling the radiation source 16, the cradle 26, and the cassette 24. The mobile X-ray image capturing apparatus 12 captures a radiation image of the patient (subject) 18 at an image capturing site, e.g., the patient's room 110.

The transmitting and receiving terminal 28 of the cassette 24 serves as a mobile station and can communicate with the server 121 in the management room 116, which serves as a radiation image information collecting facility, via the mobile hospital communication network 104 and the hospital LAN 100.

When the cassette controller 46 detects that radiation image information is stored in the image memory 82, the cassette controller 46 sends the radiation image information stored in the image memory 82 to the server 121 via the transmitting and receiving terminal 28, the mobile hospital communication network 104, and the hospital LAN 100 while the cassette 24 is moving.

In as much as the radiation image information is sent to the server 121 while the cassette 24 is moving, the radiation image information supplied from the server 121 via the hospital LAN 100 can be seen at each console 120 quickly after the radiation image information is captured. If the cassette 24 is mounted in the cradle 26 while the cassette 24 is moving, the cassette 24 can be supplied with electric power from the battery 27 of the mobile X-ray image capturing apparatus 12 for sending the captured radiation image information. At the same time, while the cassette 24 is moving, the battery 268 of the transmitting and receiving terminal 28 can be charged by the battery 27 which is of a relatively large power capacity.

After the transmitting and receiving terminal 28 has completed the transmission of the radiation image information from the image memory 82, the mobile X-ray image capturing apparatus 12 can capture radiation image information of another patient 18 in another patient's room 110, using the same cassette 24, and store the captured radiation image information in the image memory 82.

Since the radiation image information is sent to the server 121 while the mobile X-ray image capturing apparatus 12 is in motion to another image capturing site, the mobile X-ray image capturing apparatus 12 can transmit a plurality of items of radiation image information to the server 121 without delay even if the image memory 82 has a small storage capacity.

The transmitting and receiving terminal 28 also serves as an exit detecting mechanism for detecting whether the mobile X-ray image capturing apparatus 12 has moved out of the patient's room 110 or not. When the cassette controller 46 detects the movement of the mobile X-ray image capturing apparatus 12 leaving the patient's room 110 based on the detection of the communication range 122 by the transmitting and receiving terminal 28, the cassette controller 46 has the cassette 24 start sending the radiation image information to the server 121. Accordingly, no radio wave is sent to and received by the mobile X-ray image capturing apparatus 12 while it is in the patient's room 110.

The mobile hospital communication network 104 includes the base stations 124 whose communication ranges 122 overlap each other. If the transmitting and receiving terminal 28 comprises an existing mobile terminal, e.g., a PHS terminal, mounted on the mobile X-ray image capturing apparatus 12 for receiving and transmitting wireless signals, then the existing communication infrastructure can be used without the need for a new communication infrastructure for use between the mobile X-ray image capturing apparatus 12 and the radiation image information collecting facility. The mobile terminal may instead be a terminal having the same radio-wave oscillation intensity as PHS terminals.

Figure 7:
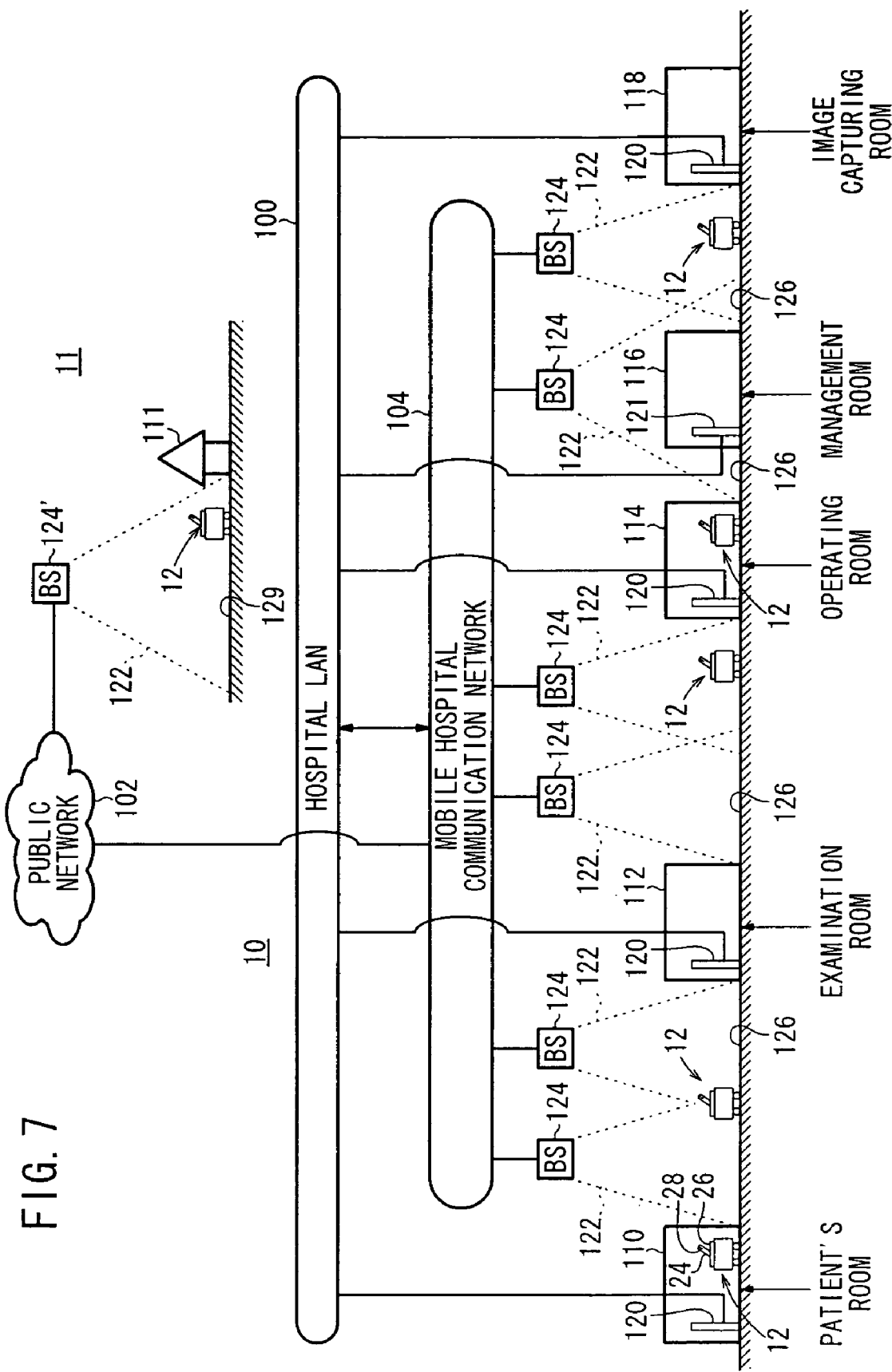
FIG. 7 is a schematic diagram, partly in block form, of a wide-area radiation image information collecting system which includes the hospital radiation image information collecting system.

FIG. 7 shows a wide-area radiation image information collecting system 11 which includes the hospital radiation image information collecting system 10 shown in FIG. 1. According to the wide-area radiation image information collecting system 11, a mobile X-ray image capturing apparatus 12 can capture radiation image at a home 111, and transfer the captured radiation image information to the image memory 138 so as to store the information therein. While the mobile X-ray image capturing apparatus 12 is moving on a road 129, the radiation image information stored in the image memory 138 is transmitted through the transmitting and receiving terminal 28, an existing base station 124', the existing public network 102, the mobile hospital communication network 104, and the hospital LAN 100 to the server 121 in the management room 116.

In other words, the image capturing site where a radiation image is captured is not limited to the operating room 114, the patient's room 110, and the examination room 112, but may be other places than the X-ray room 118, but may be a home care room at the home 111.

According to the present embodiment, as described above, the radiation image information captured and recorded in the cassette 24 by the mobile X-ray image capturing apparatus 12 at a desired location can be sent to the server 121 which serves as a radiation image collecting facility without delay.

Figure 8:
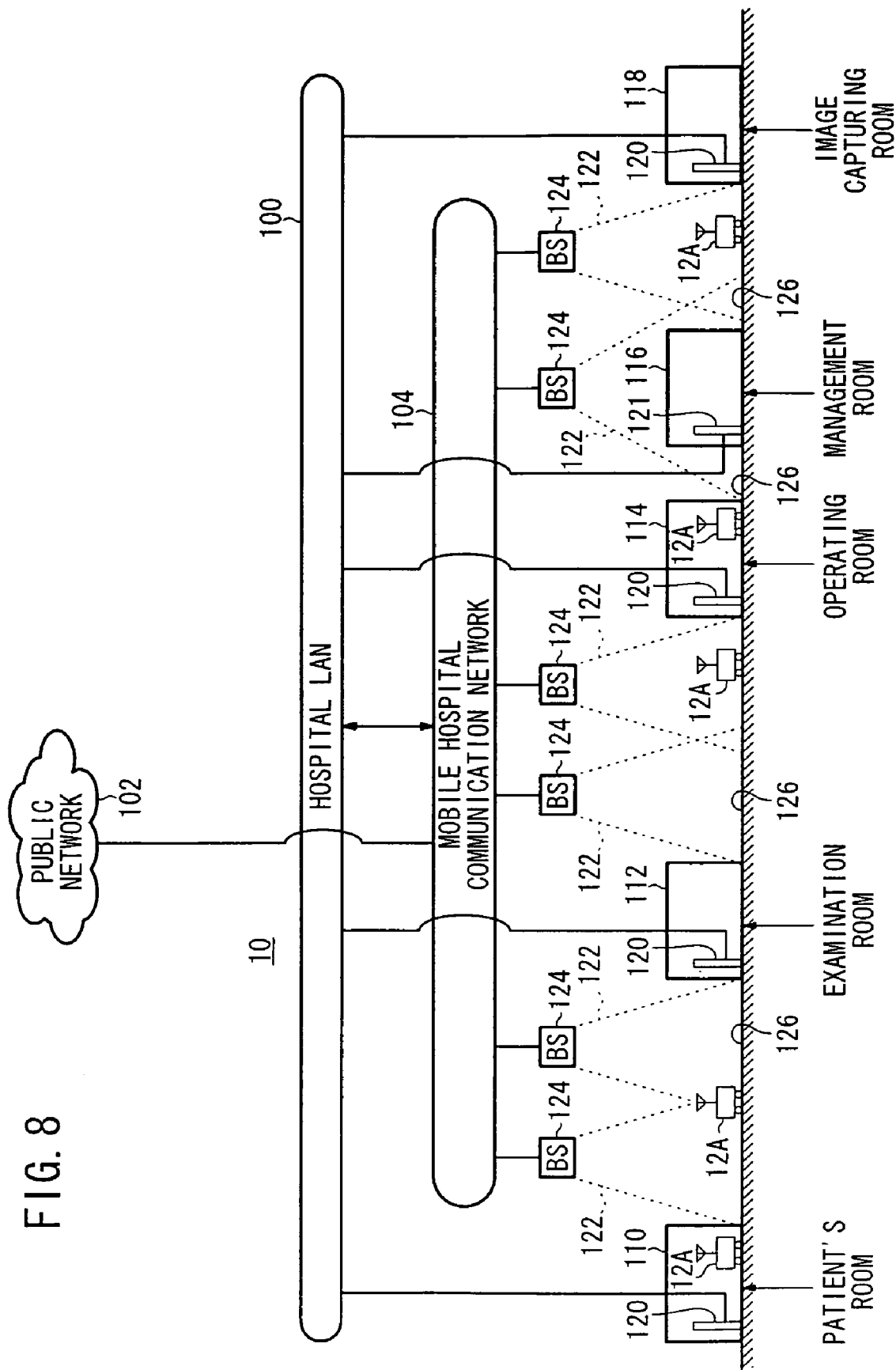
FIG. 8 is a schematic diagram, partly in block form, of a hospital radiation image information collecting system incorporating a plurality of mobile X-ray image capturing apparatus according to another embodiment of the present invention.

FIG. 8 shows a hospital radiation image information collecting system 10 incorporating a plurality of mobile X-ray image capturing apparatus 12A according to another embodiment of the present invention.

Those parts of the mobile X-ray image capturing apparatus 12A which correspond to or identical to those of the mobile X-ray image capturing apparatus 12 shown in FIG. 2 are denoted by corresponding or identical reference numerals with a suffix A, and will not be described in detail below.

Figure 9:
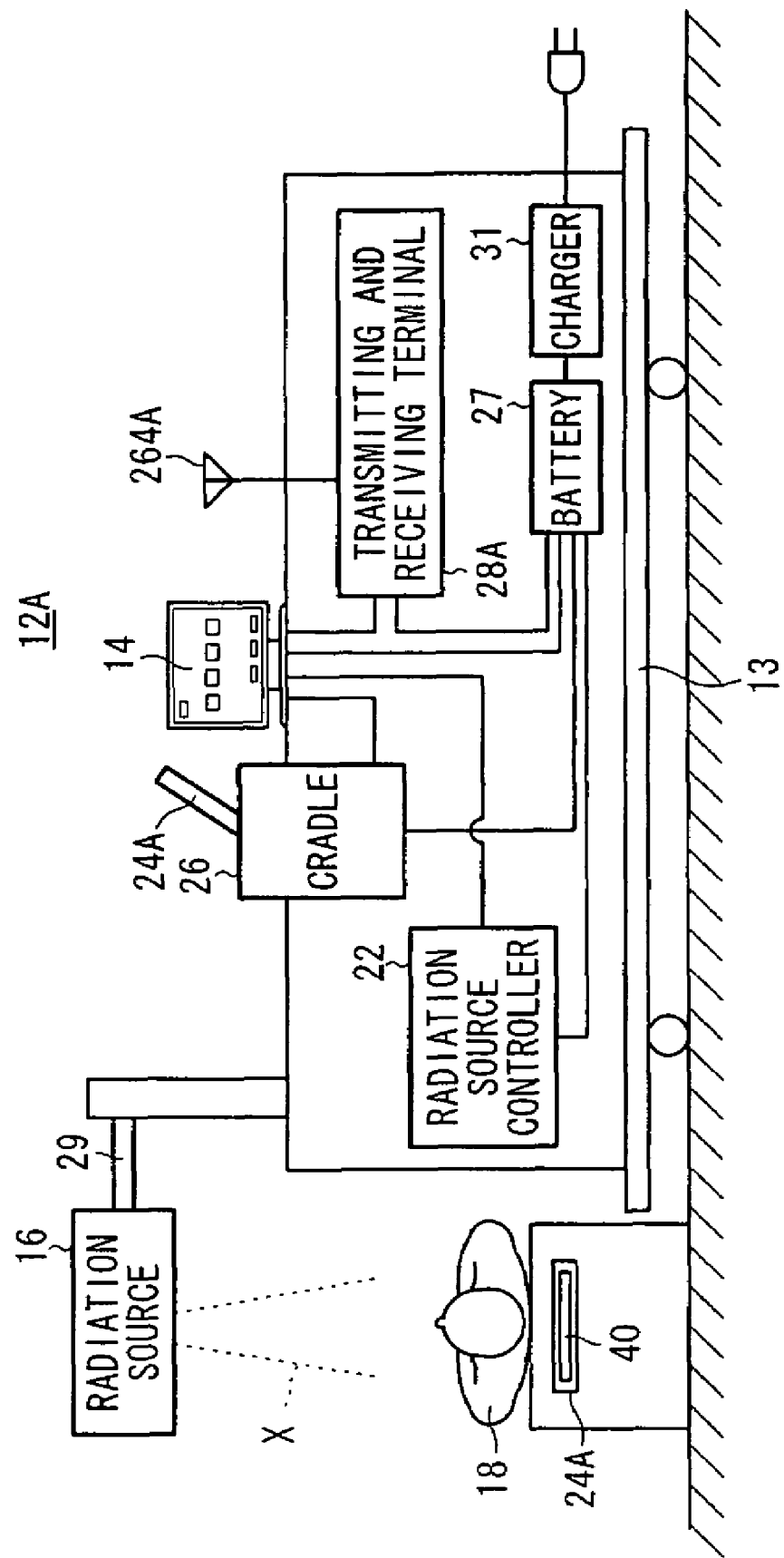
FIG. 9 is a schematic diagram, partly in block form, showing the manner in which one of the mobile X-ray image capturing apparatus shown in FIG. 8 is used in a patient's room, for example.

FIG. 9 shows the manner in which one of the mobile X-ray image capturing apparatus 12A is used in the patient's room 110, for example.

The mobile X-ray image capturing apparatus 12A placed on a carriage 13 includes a console 14 having a display panel for entering image capturing information or the like for capturing radiation image information or acquiring image capturing information or the like from the from the mobile hospital communication network 104 and the hospital LAN 100, a radiation source controller 22 for controlling a radiation source 16 according to the image capturing information supplied from the console 14A to apply a radiation X to a subject, e.g., a patient 18, a cradle (cassette mount) 26 for receiving the cassette 24 which houses a radiation detector 40 for recording radiation image information of the patient 18 when it is irradiated with the radiation X that has passed through the patient 18, a transmitting and receiving terminal 28A for sending radiation image information to the mobile hospital communication network 104 and acquiring necessary information from the mobile hospital communication network 104 by way of wireless communications, and a battery 27 for supplying electric power to the console 14, the radiation source 16, the radiation source controller 22, the cassette 24, the cradle 26, and the transmitting and receiving terminal 28A.

Figure 10:
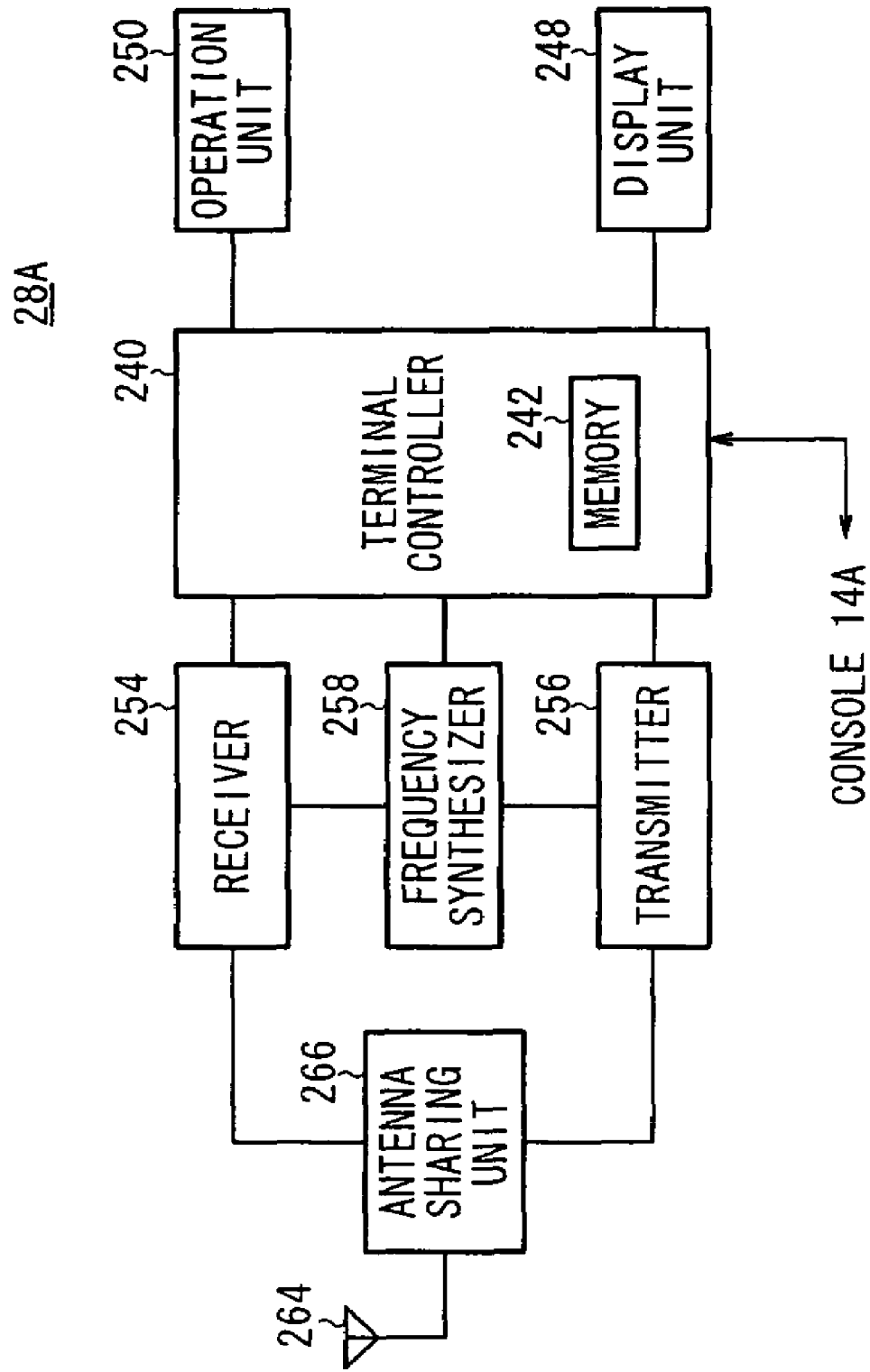
FIG. 10 is a functional block diagram of a transmitting and receiving terminal of the mobile X-ray image capturing apparatus shown in FIG. 9.

FIG. 10 shows in functional block form the transmitting and receiving terminal 28A of the mobile X-ray image capturing apparatus 12A. The transmitting and receiving terminal 28A may comprise a PHS terminal.

The transmitting and receiving terminal 28A includes a terminal controller 240. To the terminal controller 240, there is connected a transceiver 256 for modulating data (radiation image information or the like) read out from a console 14A into an intermediate-frequency signal, converting the intermediate-frequency signal into an RF signal, and sending the RF signal through the antenna sharing unit 266 to an antenna 264A, from which a radio wave based on the RF signal is radiated.

Figure 11:
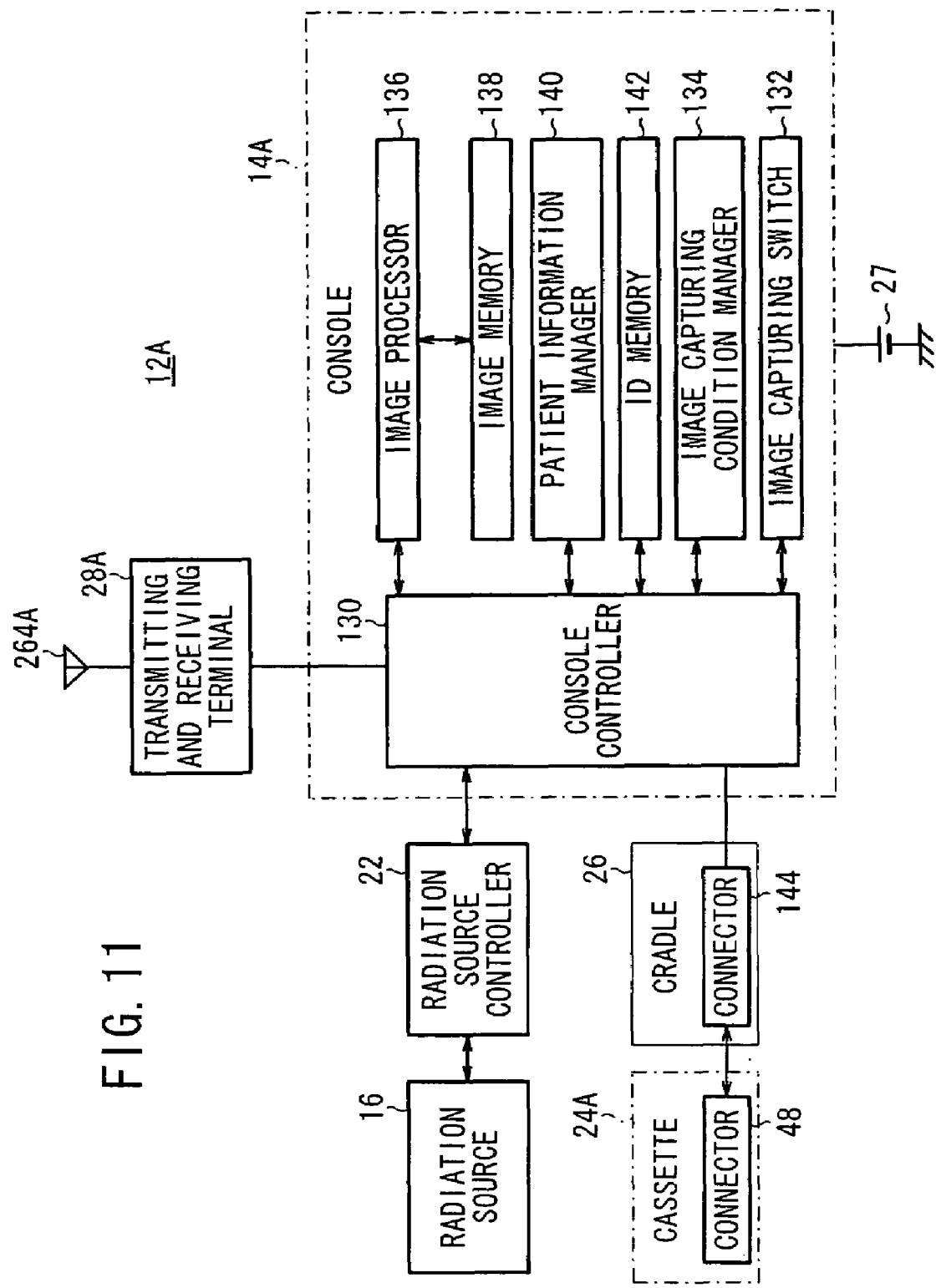
FIG. 11 is a functional block diagram of a console of the mobile X-ray image capturing apparatus shown in FIG. 9.

FIG. 11 shows in function block form the console 14A of the mobile X-ray image capturing apparatus 12A. The console 14A comprises a console controller 130, an image capturing switch 132, an image capturing condition manager 134 for managing image capturing conditions required for capturing a radiation image based on the radiation X from the radiation source 16, an image processor (image processing means) 136 for processing the radiation image information received from the cassette 24A, an image memory 138 for storing the radiation image information processed by the image processor 136, a patient information manager 140 for managing patient information of the subject (patient) 18 whose image is to be captured, and an ID memory 142 for storing ID information for identifying the mobile X-ray image capturing apparatus 12A.

The image capturing conditions refer to condition for determining a tube voltage, a tube current, an irradiation time, etc. required to apply a radiation X at an appropriate dose to an area of the patient 18 to be imaged. The image capturing conditions may include an area to be imaged, an image capturing method, etc., for example. The patient information refers to information for identifying the patient 18, such as the name, gender, patient ID number, etc. of the patient 18. Ordering information for instructing the mobile X-ray image capturing apparatus 12A to capture a radiation image, including the image capturing conditions and the patient information, can be set directly on the console 14A or can be acquired in advance from the server 121 via the hospital LAN 100 or the mobile hospital communication network 104.

The console controller 130 is connected to the cradle 26 by a connector 144 thereof. When the cassette 24A is mounted in the cradle 26, the cassette 24A is electrically connected to the connector 144 by a connector 48 thereof. The console controller 130 acquires radiation image information from the cassette 24A through the connectors 48, 144, and supplies the acquired radiation image information to the image processor 136.

Figure 12:
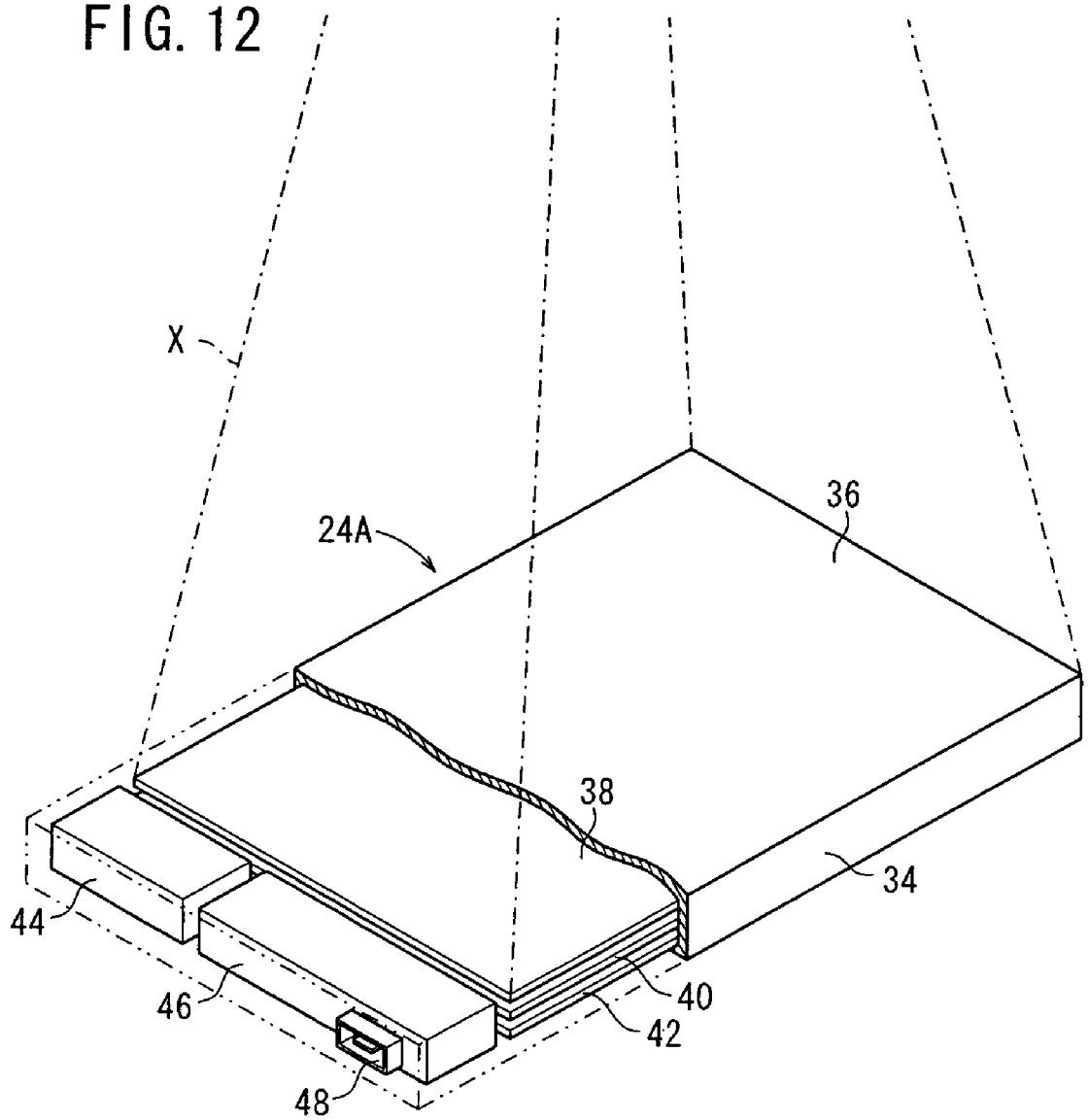
FIG. 12 is a perspective view, partly cut away, showing internal structural details of a cassette according to another embodiment of the present invention.

FIG. 12 shows in perspective internal structural details of the cassette 24A. As shown in FIG. 12, the cassette 24A has a casing 34 made of a material permeable to the radiation X. The casing 34 houses therein, in addition to the grid 38, the radiation detector 40, and the lead plate 42, a battery 44 as a power supply of the cassette 24A, a cassette controller 46 for energizing the radiation detector 40 with electric power supplied from the battery 44, and a connector 48 for sending and receiving signals including the information of the radiation X detected by the radiation detector 40 to and from the console 14A. The battery 44 of the cassette 24A can be charged by the battery 27 of the mobile X-ray image capturing apparatus 12A through the connector 144 and the connector 48.

Figure 13:
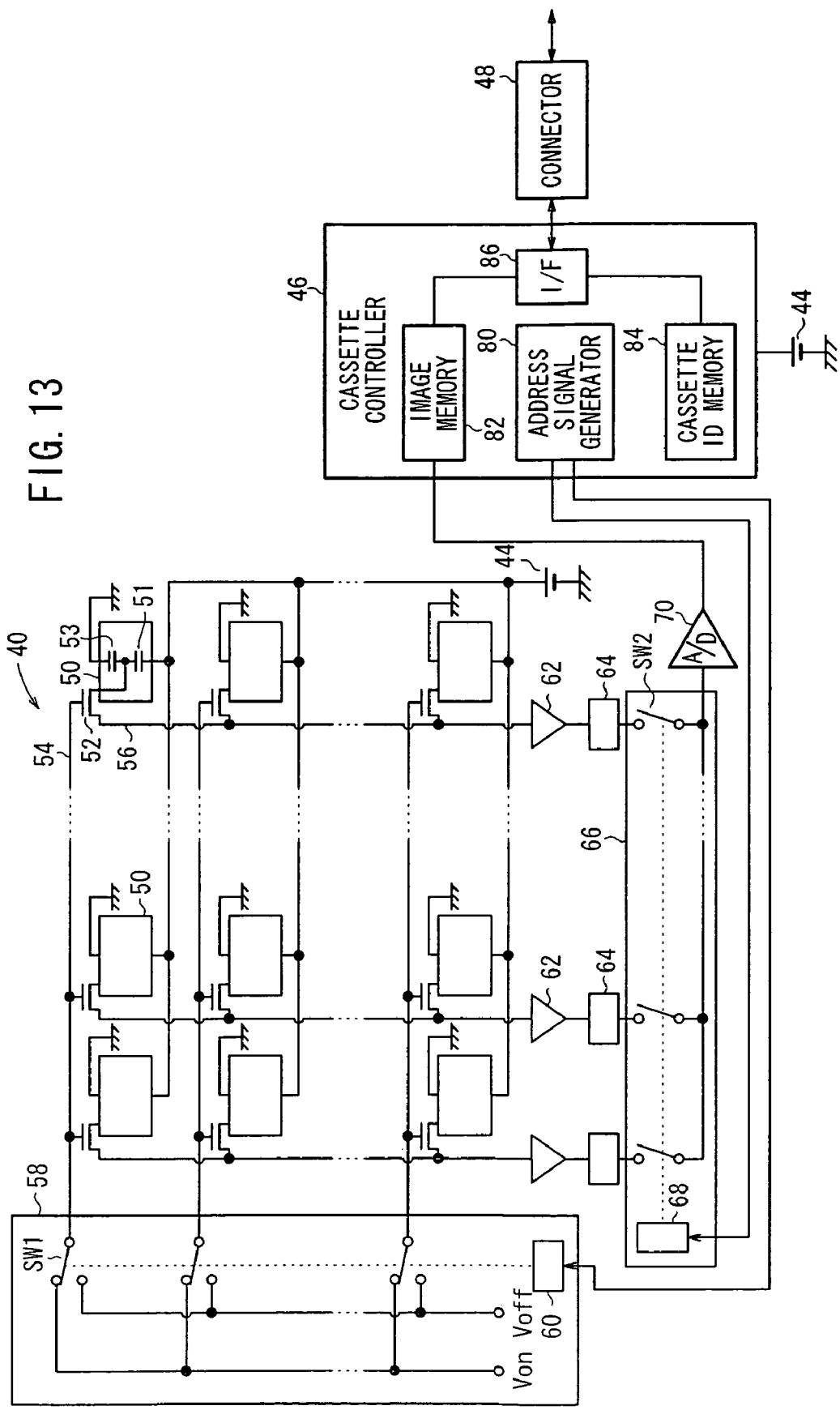
FIG. 13 is a functional block diagram of a radiation detector and a cassette controller of the cassette shown in FIG. 12.

FIG. 13 shows in block form the radiation detector 40 and the cassette controller 46 of the cassette 24A.

The cassette controller 46 includes an address signal generator 80 for supplying address signals to the address decoder 60 of the line scanning driver 58 and the address decoder 68 of the multiplexer 66 of the radiation detector 40, an image memory 82 for storing the radiation image information detected by the radiation detector 40, a cassette ID memory 84 for storing cassette ID information for identifying the cassette 24A, and an interface 86. The connector 48 receives a transmission request signal for radiation image information from the console 14A via the connector 144 of the cradle 26 and transmits the cassette ID information stored in the cassette ID memory 84 and the radiation image information stored in the image memory 82 to the console 14A.

The hospital radiation image information collecting system 10 incorporating the mobile X-ray image capturing apparatus 12A is basically constructed as described above, and the operation of the hospital radiation image information collecting system 10 will be described below.

After having captured the radiation image information, the cassette 24A is placed in the cradle 26 of the mobile X-ray image capturing apparatus 12A.

When the connectors 48, 144 are connected to each other at this time, the console controller 130 sends a transmission request signal for radiation image information to the cassette controller 46 of the cassette 24A via the connector 14.

If the image memory 82 of the cassette 24A stores radiation image information, then the cassette controller 46 reads out the radiation image information from the image memory 82 upon reception of the transmission request signal. The read radiation image information is sent to the image processor 136 through the interface 86, the connector 48, the connector 144, and the console controller 130.

The image processor 136 processes the radiation image information, and stores the processed radiation image information in the image memory 138 in association with the patient information of the patient 18 which is registered in the patient information manager 140.

The radiation image information starts being transferred from the image memory 82 of the cassette 24A to the image memory 138 of the console 14A at the time when the cassette 24A is mounted in the cradle 26. Since the patient's room 110 is not covered by the communication range 122 of the corresponding base stations 124, the radiation image information is not transferred from the image memory 138 of the console 14A through the transmitting and receiving terminal 28A to the mobile hospital communication network 104 as long as the mobile X-ray image capturing apparatus 12A is positioned in the patient's room 110.

When the mobile X-ray image capturing apparatus 12A moves out of the patient's room 110 and the transmitting and receiving terminal 28A enters the communication range 122 of the corresponding base stations 124 of the mobile hospital communication network 104, or, in other words, when the transmitting and receiving terminal 28A detects a predetermined radio-wave intensity from the base station 124, the transmitting and receiving terminal 28A indicates the detection of the predetermined radio-wave intensity to the console controller 130.

The console controller 130 then reads out the radiation image information from the image memory 138 and transfers the read radiation image information to the terminal controller 240 of the transmitting and receiving terminal 28A. The terminal controller 240 sends the radiation image information sent from the image memory 138 through the transmitter 256, the antenna sharing unit 266, and the antenna 264A to the base station 124. The base station 124 transfers the received radiation image information to the server 121 in the management room 116 via the mobile hospital communication network 104 and the hospital LAN 100.

The radiation image information transferred to the server 121 can immediately be sent through the hospital LAN 100 and used for examination by the doctor or the like who handles the console 120 in the examination room 112, for example.

As shown in FIG. 8, since the communication ranges 122 of adjacent ones of the base stations 124 overlap each other while the mobile X-ray image capturing apparatus 12A is moving down the aisle or aisles 126 from the patient's room 110 to the examination room 112 or to another patient's room 110, not shown, the mobile X-ray image capturing apparatus 12A can switch successively to communication ranges 122 of greater radio-wave intensities. Accordingly, the mobile X-ray image capturing apparatus 12A can transfer the radiation image information reliably to the server 121 without communication interruptions while being in motion down the aisle or aisles 126. When the mobile X-ray image capturing apparatus 12A captures radiation image information in another patient's room 110, the captured radiation image information can thus be stored in the image memory 82 of the same cassette 24, overwriting any existing radiation image information. The image memory 82 of the cassette 24 is usually of a storage capacity for recording the radiation image information only for one sheet of radiation image.

Whether the mobile X-ray image capturing apparatus 12A is in the patient's room 110 or not, i.e., whether the mobile X-ray image capturing apparatus 12A has moved out of the patient's room 110 or not can be determined not only based on the communication range 122, but an exit detecting mechanism comprising an RFID card attached to the mobile X-ray image capturing apparatus 12A and an RFID card reader attached to the patient's room 110 near its door.

According to the above embodiment, as described above, the mobile X-ray image capturing apparatus 12A includes the radiation source 16, the cradle 26 serving as a mount for the cassette 24A which includes the radiation detector 40 for detecting the radiation X that has emitted from the radiation source 16 and passed through the subject, and storing the detected radiation image information, the image memory 138, the transmitting and receiving terminal 28A, and the console controller 130 for controlling the radiation source 16, the cradle 26, the image memory 138, and the transmitting and receiving terminal 28A. The mobile X-ray image capturing apparatus 12A captures a radiation image of the patient (subject) 18 in an image capturing site, e.g., the patient's room 110.

The transmitting and receiving terminal 28A serves as a mobile station and can communicate with the server 121 in the management room 116, which serves as a radiation image information collecting facility, via the mobile hospital communication network 104 and the hospital LAN 100. When the console controller 130 detects, based on the transmission request signal, that the radiation image information is stored in the cassette 24A mounted in the cradle 26, the console controller 130 transfers the radiation image information from the cassette 24A through the cradle 26 to the image memory 138, which stores the transmitted radiation image information. While the mobile X-ray image capturing apparatus 12A which has moved out of the patient's room 110 is moving down the aisle or aisles 126, the mobile X-ray image capturing apparatus 12A sends the radiation image information stored in the image memory 138 to the server 131 through the transmitting and receiving terminal 28A, the mobile hospital communication network 104, and the hospital LAN 100.

As described above, when the console controller 130 of the mobile X-ray image capturing apparatus 12A detects, based on the transmission request signal, that the radiation image information is stored in the cassette 24A mounted in the cradle 26 of the mobile X-ray image capturing apparatus 12A, the console controller 130 transfers the radiation image information from the cassette 24A through the cradle 26 to the image memory 138, which stores the transmitted radiation image information. While the mobile X-ray image capturing apparatus 12A is moving down, it sends the radiation image information stored in the image memory 138 to the server 121 through the transmitting and receiving terminal 28A and the mobile hospital communication network 104. Accordingly, the cassette 24A is not required to have a wireless communication function and hence may have a small power requirement. The cassette 24A can thus be small in size and weight and can be carried around with ease.

In as much as the radiation image information is sent to the server 121 while the mobile X-ray image capturing apparatus 12A is moving, the radiation image information supplied from the server 121 can be seen quickly after the radiation image information is captured.

The mobile X-ray image capturing apparatus 12A has the transmitting and receiving terminal 28A which can also be used as an exit detecting mechanism for detecting that the mobile X-ray image capturing apparatus 12A has moved out of the patient's room 110. The console controller 130 starts to send the radiation image information to the server 121 when the transmitting and receiving terminal 28A detects that the mobile X-ray image capturing apparatus 12A has moved out of the patient's room 110 by detecting the communication range 122. Therefore, no radio waves are sent and received in the patient's room 110.

The mobile hospital communication network 104 includes the base stations 124 whose communication ranges 122 overlap each other. If the transmitting and receiving terminal 28A comprises an existing mobile terminal, e.g., a PHS terminal, mounted on the mobile X-ray image capturing apparatus 12A for receiving and transmitting wireless signals, then the existing communication infrastructure can be used without the need for a new communication infrastructure for use between the mobile X-ray image capturing apparatus 12A and the radiation image information collecting facility. The mobile terminal may instead be a terminal having the same radio-wave oscillation intensity as PHS terminals.

Figure 14:
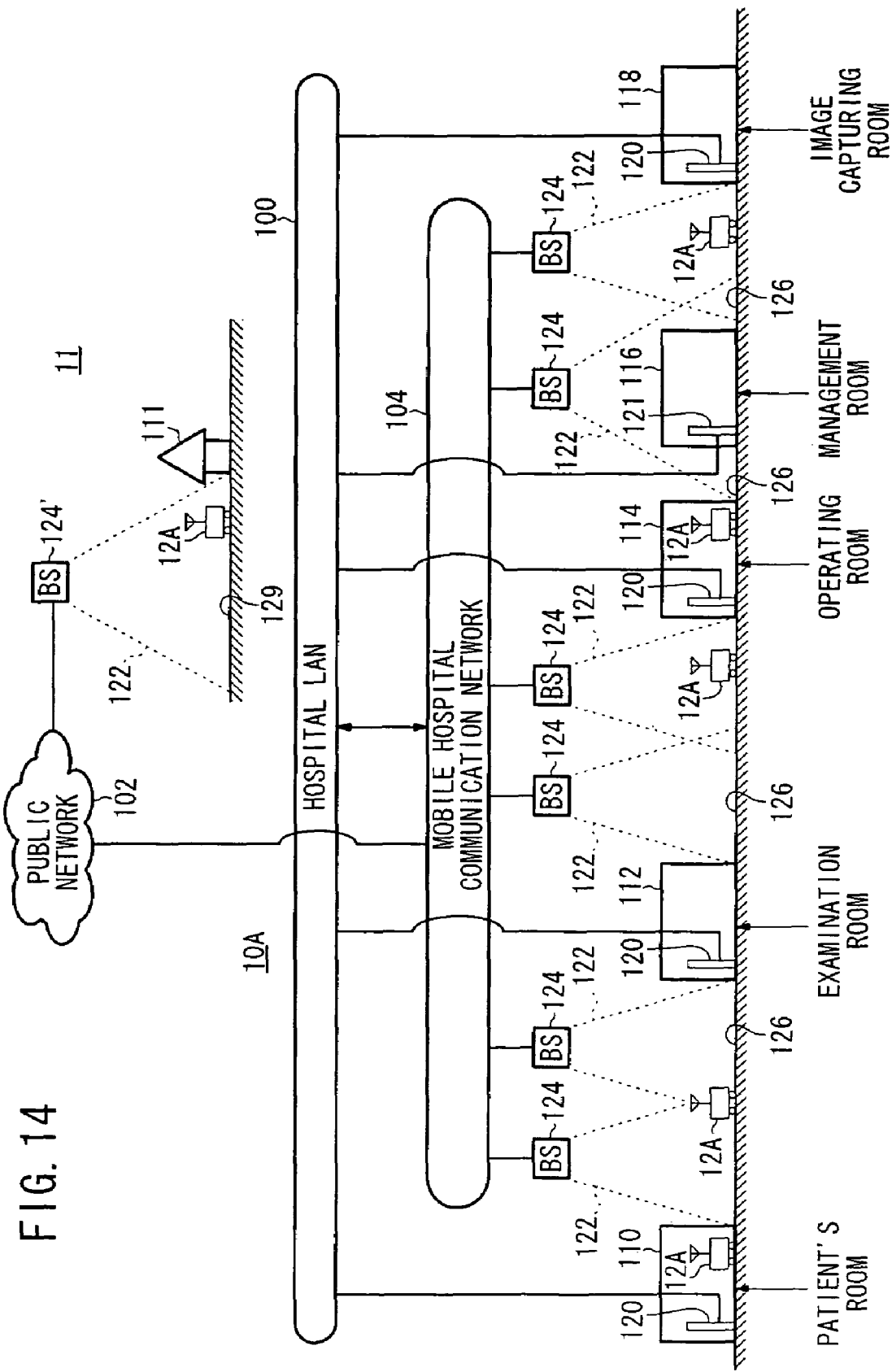
FIG. 14 is a schematic diagram, partly in block form, of a wide-area radiation image information collecting system which includes the hospital radiation image information collecting system.

FIG. 14 shows a wide-area radiation image information collecting system 11. According to the wide-area radiation image information collecting system 11, a mobile X-ray image capturing apparatus 12A can capture radiation image information at a home 111. Specifically, when a radiation image is captured at the home 111, the captured radiation image information is transferred to and stored in the image memory 138. While the mobile X-ray image capturing apparatus 12A is moving on a road 129, the radiation image information stored in the image memory 138 is transmitted through the console controller 130, the transmitting and receiving terminal 28A, an existing base station 124', the existing public network 102, the mobile hospital communication network 104, and the hospital LAN 100 to the server 121 in the management room 116.

In other words, the image capturing site where a radiation image is captured is not limited to the operating room 114, the patient's room 110, and the examination room 112, but may be other places such as a home care room at the home 111 than the X-ray room 118.

According to the other embodiment described above, the radiation image information captured and recorded in the cassette 24A by the mobile X-ray image capturing apparatus 12A at a desired location can be sent to the server 121 which serves as a radiation image collecting facility without delay. In addition, the cassette 24A can be small and light in weight.

The present invention is not limited to the above two embodiments, but changes and modifications may be made thereto within the scope of the invention.

For example, the radiation detector 40 housed in the cassettes 24, 24A directly converts the dose of the applied radiation X into an electric signal with the pixels 50 serving as photoelectric transducers. However, the mobile X-ray image capturing apparatus may employ a radiation detector including a scintillator for converting the applied radiation X into visible light and a solid-state detecting device such as of amorphous silicon (a-Si) or the like for converting the visible light into an electric signal (see Japanese patent No. 3494683).

Alternatively, a light-conversion radiation detector can be utilized for acquiring radiation image information. The light-conversion radiation detector operates as follows: When a radiation is applied to a matrix of solid-state detecting devices, the solid-state detecting devices store an electrostatic latent image depending on the dose of the applied radiation. For reading the stored electrostatic latent image, reading light is applied to the solid-state detecting devices to cause the solid-state detecting devices to generate an electric current representing radiation image information. When erasing light is applied to the radiation detector, radiation image information representing a residual electrostatic latent image is erased from the radiation detector, which can thus be reused (see Japanese Laid-Open Patent Publication No. 2000-105297).

Furthermore, communication frames, each comprising a plurality of slots, are sent and received between the base stations 124 and the transmitting and receiving terminal 28 of the cassette 24 at frame transmission timings that are shifted slot by slot based on a synchronizing signal used between all the base stations 124, and the communication ranges 122 of adjacent ones of the base stations 124 overlap each other, with the base stations 124 using different frequencies. All the base stations 124 are timing-controlled to send communication frames such that at the timing of the final intraframe slot of a base station 124 which is positioned behind the cassette 24 (the transmitting and receiving terminal 28) with respect to the direction in which the cassette 24 travels, the first intraframe slot of a next base station 124 is transmitted. The transmitting and receiving terminal 28 not only sends and receives communication frames, but also tries to receive signals from other base stations 124 in the final slots of the communication frames. If the transmitting and receiving terminal 28 judges that it can communicate with another base station 124, then it changes the base station 124 to communicate with. Accordingly, the transmitting and receiving terminal 28 can send the radiation image information reliably without interruptions to the server 121 in the management room 116.

When the cassettes 24, 24A are used in the operating room 114 or the like, blood stains and contaminants may be applied to the cassettes 24, 24A. The cassettes 24, 24A may be of a water-resistant, sealed structure so that they can be sterilized and cleaned to remove such blood stains and contaminants for repetitive use.

Figure 15:
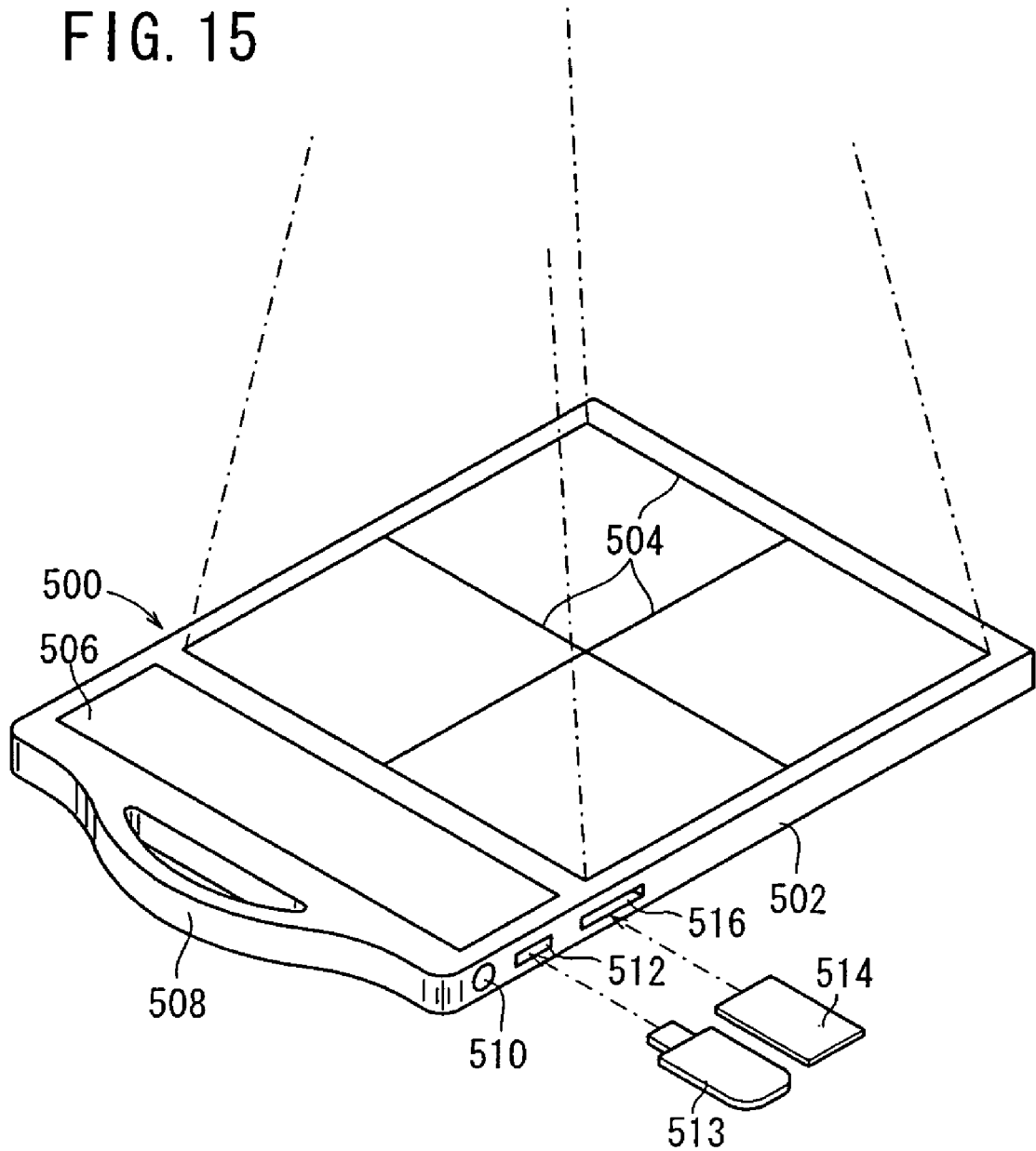
FIG. 15 is a perspective view of a cassette according to still another embodiment of the present invention.

FIG. 15 shows in perspective a cassette 500 according to still another embodiment of the present invention.

As shown in FIG. 15, the cassette 500 has guide lines 504 drawn on the irradiated surface of a casing 502 as a reference mark for an image capturing area and an image capturing position. Using the guide lines 504, the subject to be imaged, such as the patient 18, can be positioned with respect to the cassette 500 and the range in which the radiation is to be applied to the cassette 500 can be determined, for thereby recording radiation image information in an appropriate image capturing area of the cassette 500.

The cassette 500 also has a display unit 506 outside of the image capturing area thereof for displaying various items of information about the cassette 500. Specifically, the display unit 506 displays ID information of the subject, e.g., the patient 18, whose radiation image is recorded in the cassette 500, the number of times that the cassette 500 has been used, an accumulated exposed dose, the charged state (remaining power level) of the battery 44 housed in the cassette 500, image capturing conditions for radiation image information, and a positioning image representing the patient 18 positioned with respect to the cassette 500, etc. The radiological technician can confirm the patient 18 based on the ID information displayed on the display unit 506, also confirm in advance that the cassette 500 is in a usable state, position the desired area to be imaged of the patient 18 with respect to the cassette 500 based on the displayed positioning image, and capture optimum radiation image in the cassette 500.

The cassette 500 includes a handle 508 to be gripped by the user to handle and carry the cassette 500 with ease.

The cassette 500 also has an input terminal 510 for connection to an AC adapter, a USB (Universal Serial Bus) terminal 512, and a card slot 516 for receiving a memory card 514, all provided on a side wall of the casing of the cassette 500.

When the charging function of the battery 44 housed in the cassette 500 is low or when there is not enough time to charge the battery 44, an AC adapter is connected to the input terminal 510 to supply electric power from an external source for thereby making the cassette 500 immediately operable.

The USB terminal 512 or the card slot 516 can be used when the cassette 500 is unable to send and receive information to and from an external device such as the console 14A or the like by way of wireless communications. Specifically, a USB memory 513 is attached to the USB terminal 512, and necessary information from the cassette 500 is recorded into the USB memory 513. Then, the USB memory 513 is detached from the USB terminal 512, and attached to the external device so as to transfer the information to the external device. Alternatively, the memory card 514 is inserted into the card slot 516 and necessary information from the cassette 500 is recorded into the memory card 514. Thereafter, the memory card 514 is removed from the card slot 516 and inserted to the external device to send the information to the external device.

Figure 16:
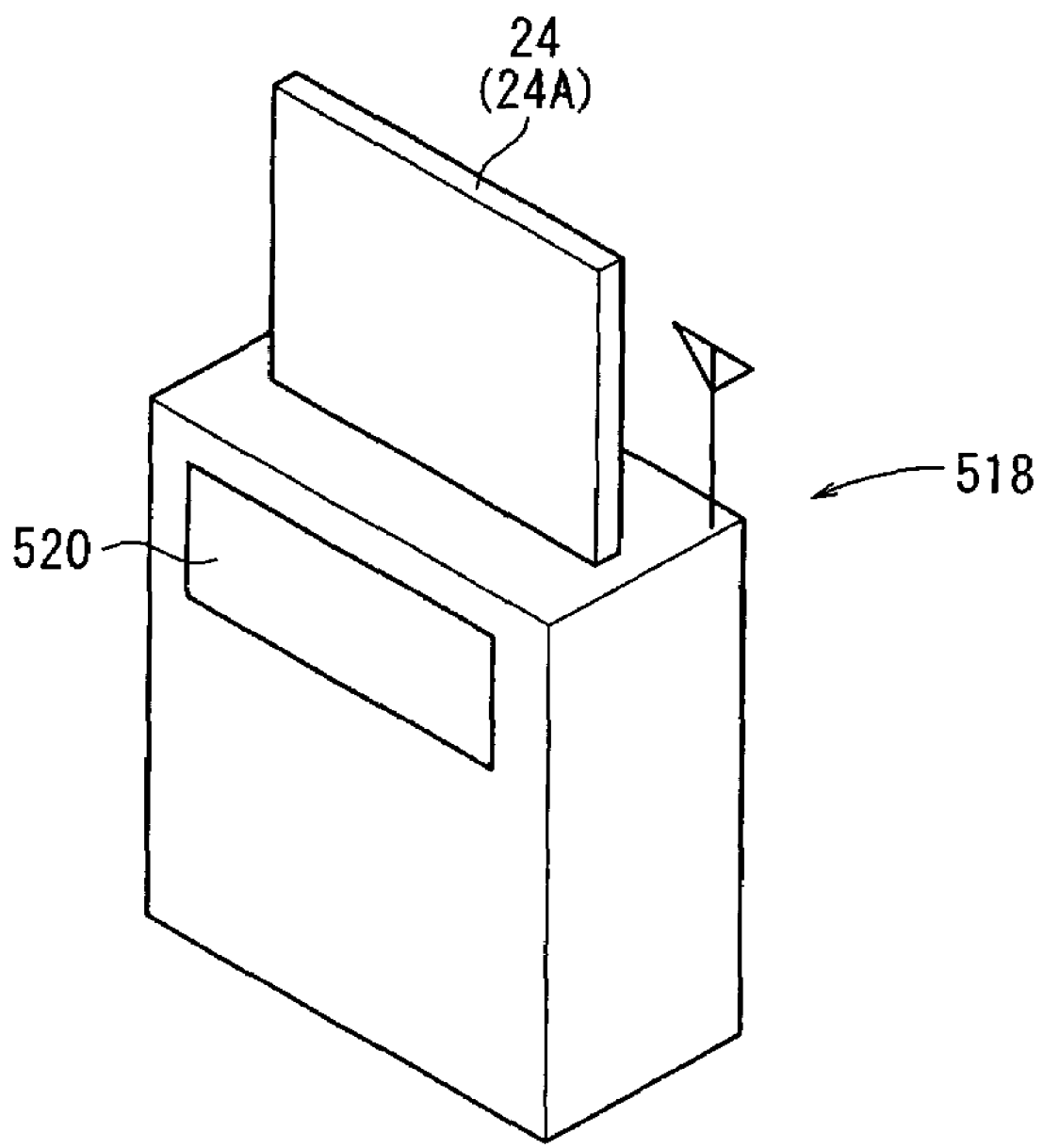
FIG. 16 is a perspective view of a cradle for charging a battery in the cassette.

FIG. 16 shows a cradle 518 for receiving the cassette 24, 24A and charging the battery 44 housed in the cassette 24, 24A. The cradle 518 is positioned in the operating room 112, the image capturing room 118, or a desired location in the hospital. The cradle 518 may not only be able to charge the battery 44, but also have a wireless or wired communication function to send and receive necessary information to and from the server 121 through the base stations 124, the mobile hospital communication network 104, and the hospital LAN 100. The information that is sent from the cradle 518 may include radiation image information recorded in the cassette 24, 24A loaded in the cradle 518.

The cradle 518 has a display unit 520 for displaying the charged state of the battery 44 housed in the cassette 24, 24A and necessary information including radiation image information acquired from the cassette 24, 24A.

A plurality of cradles 518 may be connected to the hospital LAN 100, and charged states of the batteries 44 housed in the cassettes 24, 24A loaded in the respective cradles 518 may be retrieved from the consoles 120 and the server 121 through the hospital LAN 100, so that the user can confirm the locations of any cassettes 24, 24A whose batteries 44 are sufficiently charged, based on the retrieved charged states of the batteries 4.

Although certain preferred embodiments of the present invention have been shown and described in detail, it should be understood that various changes and modifications may be made therein without departing from the scope of the appended claims.

What is claimed is:

1. A cassette comprising:
   a radiation detector for detecting a radiation that has passed through a subject, and converting the detected radiation into radiation image information;
   an image memory for storing the converted radiation image information therein;
   a transmitting and receiving terminal; and
   a controller for controlling said radiation detector, said image memory, and said transmitting and receiving terminal;
   wherein said transmitting and receiving terminal serves as a mobile station and communicates with a radiation image information collecting facility through a mobile communication network; and
   when said controller detects that said radiation image information is stored in said image memory, said controller transmits said radiation image information stored in said image memory to said radiation image information collecting facility via said transmitting and receiving terminal and said mobile communication network, while the cassette is moving.

2. A cassette according to claim 1, wherein said mobile communication network includes a plurality of base stations having partially overlapping communication ranges, and said transmitting and receiving terminal comprises a mobile terminal capable of sending and receiving signals by way of wireless communications.

3. A mobile X-ray image capturing apparatus a cassette comprising:
   a radiation detector for detecting a radiation that has passed through a subject, and converting the detected radiation into radiation image information;
   an image memory for storing the converted radiation image information therein;
   a transmitting and receiving terminal; and
   a controller for controlling said radiation detector, said image memory, and said transmitting and receiving terminal;
   wherein said transmitting and receiving terminal serves as a mobile station and communicates with a radiation image information collecting facility through a mobile communication network; and
   when said controller detects that said radiation image information is stored in said image memory, said controller transmits said radiation image information stored in said image memory to said radiation image information collecting facility via said transmitting and receiving terminal and said mobile communication network, while the cassette is moving,
   wherein said mobile communication network includes a plurality of base stations having partially overlapping communication ranges, and said transmitting and receiving terminal comprises a mobile terminal capable of sending and receiving signals by way of wireless communications; and
   a mount for receiving removably the cassette therein and supplying electric power to said cassette.

4. A mobile X-ray image capturing apparatus a cassette comprising:
- a radiation detector for detecting a radiation that has passed through a subject, and converting the detected radiation into radiation image information;
- an image memory for storing the converted radiation image information therein;
- a transmitting and receiving terminal; and
- a controller for controlling said radiation detector, said image memory, and said transmitting and receiving terminal;
- wherein said transmitting and receiving terminal serves as a mobile station and communicates with a radiation image information collecting facility through a mobile communication network; and
- when said controller detects that said radiation image information is stored in said image memory, said controller transmits said radiation image information stored in said image memory to said radiation image information collecting facility via said transmitting and receiving terminal and said mobile communication network, while the cassette is moving, and
- a mount for receiving removably the cassette therein and supplying electric power to said cassette.

5. A mobile X-ray image capturing apparatus for capturing a radiation image of a subject at a room where an image is to be captured, comprising:
- a radiation source for applying a radiation to the subject;
- a mount for receiving therein a cassette having a radiation detector for detecting the applied radiation that has passed through the subject, converting the detected radiation into radiation image information and storing the radiation image information;
- an image memory;
- a transmitting and receiving terminal; and
- a controller for controlling said radiation source, said mount, said image memory, and said transmitting and receiving terminal;
- wherein said transmitting and receiving terminal serves as a mobile station and communicates with a radiation image information collecting facility through a mobile communication network; and
- when said controller detects that said radiation image information is stored in said cassette mounted in said mount, said controller transfers said radiation image information from said cassette via said mount to said image memory for storing the radiation image information therein; and
- while said mobile X-ray image capturing apparatus is moving, said radiation image information stored in said image memory is transmitted to said radiation image information collecting facility via said transmitting and receiving terminal and said mobile communication network.

6. A mobile X-ray image capturing apparatus according to claim 5, further comprising:
- an exit detecting mechanism for detecting that said mobile X-ray image capturing apparatus has moved out of said room;
- wherein said controller starts transmitting said radiation image information to said radiation image information collecting facility when said exit detecting mechanism detects that said mobile X-ray image capturing apparatus has moved out of said room.

7. A mobile X-ray image capturing apparatus according to claim 5, wherein said mobile communication network includes a plurality of base stations having partially overlapping communication ranges, and said transmitting and receiving terminal comprises an existing mobile terminal mounted in said mobile X-ray image capturing apparatus and capable of sending and receiving signals by way of wireless communications.

8. A mobile X-ray image capturing apparatus according to claim 5, wherein said room comprises a room other than an X-ray image capturing room, including an operating room, a patient's room, a diagnosis and treatment room, and a home care room.

* * * * *

UNITED STATES PATENT AND TRADEMARK OFFICE
CERTIFICATE OF CORRECTION

| | |
|---|---|
| PATENT NO. | : 7,764,765 B2 |
| APPLICATION NO. | : 12/219598 |
| DATED | : July 27, 2010 |
| INVENTOR(S) | : Yasunori Ohta et al. |

It is certified that error appears in the above-identified patent and that said Letters Patent is hereby corrected as shown below:

- Column 20, line 37, the word "comprising:" was omitted, and the line should read --A mobile X-ray image capturing apparatus comprising: a cassette--.

-- Column 21, line 1, the word "comprising:" was omitted, and the line should read --A mobile X-ray image capturing apparatus comprising: a cassette--.

Signed and Sealed this
Twenty-first Day of June, 2011

David J. Kappos
*Director of the United States Patent and Trademark Office*